US008663679B2

(12) United States Patent
Rushlow et al.

(10) Patent No.: US 8,663,679 B2
(45) Date of Patent: Mar. 4, 2014

(54) COMPOSITIONS FOR IMPROVING BREAST HEALTH IN WOMEN

(75) Inventors: Keith E. Rushlow, Pickerington, OH (US); Robert A. Shalwitz, Bexley, OH (US); Terrence B. Mazer, Reynoldsburg, OH (US); Normanella T. Dewille, Columbus, OH (US); Tapas Das, Worthington, OH (US); Anand Seth, Dublin, OH (US)

(73) Assignee: Abbott Laboratories, Abbott Park, IL (US)

( * ) Notice: Subject to any disclaimer, the term of this patent is extended or adjusted under 35 U.S.C. 154(b) by 1663 days.

(21) Appl. No.: 11/117,236

(22) Filed: Apr. 28, 2005

(65) Prior Publication Data

US 2006/0034944 A1 Feb. 16, 2006

Related U.S. Application Data

(60) Provisional application No. 60/566,625, filed on Apr. 29, 2004, provisional application No. 60/629,789, filed on Nov. 19, 2004.

(51) Int. Cl.
*A61K 47/00* (2006.01)
*A61K 31/20* (2006.01)
*A23L 1/30* (2006.01)
*A61K 38/00* (2006.01)

(52) U.S. Cl.
USPC ........... 424/439; 514/19.4; 514/558; 426/648

(58) Field of Classification Search
None
See application file for complete search history.

(56) References Cited

U.S. PATENT DOCUMENTS

| | | | |
|---|---|---|---|
| 5,223,285 A * | 6/1993 | DeMichele et al. ............ 426/72 |
| 5,589,198 A | 12/1996 | Eskin et al. | |
| 5,612,074 A | 3/1997 | Leach | |
| 5,830,887 A | 11/1998 | Kelly | |
| 5,895,652 A | 4/1999 | Giampapa | |
| 5,900,255 A | 5/1999 | Ohta et al. | |
| 5,922,704 A * | 7/1999 | Bland ............................ 514/185 |
| 5,952,314 A * | 9/1999 | DeMichele et al. ............ 514/54 |
| 5,973,224 A * | 10/1999 | Fuchs et al. .................... 424/736 |
| 6,019,970 A | 2/2000 | Ghent et al. | |
| 6,326,355 B1 * | 12/2001 | Abbruzzese et al. ........... 514/23 |
| 6,340,703 B1 | 1/2002 | Kelly | |
| 6,355,250 B1 | 3/2002 | Patel et al. | |
| 6,375,994 B1 | 4/2002 | Paul et al. | |
| 6,391,309 B1 | 5/2002 | Empie et al. | |
| 6,436,446 B1 | 8/2002 | Forusz et al. | |
| 6,551,630 B2 | 4/2003 | Patel et al. | |
| 6,638,540 B2 | 10/2003 | Muhlbauer | |
| 2002/0192310 A1 | 12/2002 | Bland et al. | |
| 2004/0219188 A1* | 11/2004 | Comer et al. .................. 424/439 |

FOREIGN PATENT DOCUMENTS

| | | | |
|---|---|---|---|
| CA | 2158591 | 3/1996 | |
| CA | 2564592 | 5/2013 | |
| EP | 0440307 A2 | 8/1991 | |
| EP | 0 707 850 * | 4/1996 | ............. A61K 31/20 |
| EP | 0707850 A1 | 4/1996 | |
| EP | 0799578 A2 | 10/1997 | |
| JP | 1120275 | 5/1989 | |
| WO | WO 99/07239 | 2/1999 | |
| WO | WO 00/10402 | 3/2000 | |
| WO | WO 01/78783 A3 | 10/2001 | |
| WO | WO 02/052954 A3 | 7/2002 | |
| WO | 02094035 A1 | 11/2002 | |
| WO | 2005/115472 | 12/2005 | |

OTHER PUBLICATIONS

Cann et al. "Hypothesis: Iodine, selenium and the development of breast cancer" Cancer Causes & Control; 11:121-127 (2000).*
Cann et al., Cancer Causes and Control; (2000); vol. 11, pp. 121-127.*
2004 National Academy of Sciences dietary data (Dietary Reference Intakes (DRIs): Recommended Intakes for Individuals, Elements); (wbesite: www. nap.edu.*
Materna® Centrum Vitamin/Mineral listings, sources and amounts (2004); 1 pg. pdf.*
Materna® Centrum Vitamin/Mineral listings, sources and amounts (2011); 1 pg. pdf.*
http://www.centrum.co.za/product_materna.htm; downloaded Apr. 25, 2012.*
www.nutristrategy.com/nutrition/calories.htm; downloaded Sep. 9, 2013.*
Lockwood, et al., "Apparent Partial Remission of Breast Cancer in 'High Risk' Patients Supplemented With Nutritional Antioxidants, Essential Fatty Acids and Coenzyme Q10," Molecular Aspects of Medicine, vol. 15, pp. S231-S240 (1994).
Kowalska, et al., "Increased Rates of Chromosome Breakage in BRCA1 Carriers Are Reduced by Oral Selenium Supplementation," European J. of Cancer, vol. 2, No. 3, p. 186 (2004).
Gesch, et al., "Influence of Supplementary Vitamins, Minerals and Essential Fatty Acids on the Antisocial Behaviour of Young Adult Prisoners. Randomised, Placebo-Controlled Trial." The British J. of Pyschiatry; The J. of Mental Science, vol. 181, pp. 22-28.
International Preliminary Report on Patentability for PCT/US05/14595, dated Nov. 1, 2006.

(Continued)

*Primary Examiner* — Robert A Wax
*Assistant Examiner* — Jeffrey T Palenik
(74) *Attorney, Agent, or Firm* — Calfee, Halter & Griswold LLP

(57) ABSTRACT

Disclosed are compositions and corresponding methods for treating fibrocystic breast disease or other breast-related disease or condition. The compositions comprise, per serving or dose, from zero to about 400 µg selenium, from about 100 mg to about 6000 mg gamma linolenic acid, and about 0.15 mg to about 5 mg iodine, with nutritional embodiments further comprising one or more of protein, fat, carbohydrate, vitamins, and minerals and providing from about 50 to about 1000 kcal of energy per severing or dose. Also disclosed are in-vitro studies showing that certain combinations of gamma linolenic acid, iodine, and/or selenium may 1) inhibit breast cancer or fibrocystic cell proliferation, 2) reinforce the function of tight junctions of endothelial cells and of mammary epithelial cells in estrogen-sensitive conditions, and 3) reduce the risk of vascular invasion by breast cancer cells.

53 Claims, 16 Drawing Sheets

(56) References Cited

OTHER PUBLICATIONS

Office action for Canadian Application No. 2,564,592 dated Nov. 14, 2011.
"Nutrient data for 09032, Apricots, dried, sulfured, uncooked," http://ndb.nal.usda.gov/ndb/foods/show/2252, accessed Jan. 30, 2012.
"Nutrient data for 09041, Bananas, dehydrated, or banana powder," http://ndb.nal.usda.gov/ndb/foods/show/2261, accessed Jan. 30, 2012.
"Selenium May Prevent Breast Cancer," LamMA.com, Insider's Guide to Natural Medicine, printed Dec. 8, 2003.
"Medical College of Wisconsin researchers discover and test new class of anti-cancer drugs," www.mcw.edu, printed Dec. 10, 2003.
C.A. Gateley, et al, (1992) "Drug treatments for mastalgia: 17 years experience in the Cardiff mastalgia clinic," Royal Society of Medicine.
Nwankwo, et al, (2001), "Peroxisome proliferator-activiated receptor-y expression in human malignant and normal brain, breast and prostate-derived cells," Prostaglandins, Leukotrienes and Essential Fatty Acids, 64(4 & 5), 241-245.
Christodoulakos, et al, (2003), "The effect of various regimens of hormone replacement therapy on mammographic breast density," The European Menopause Journal, Maturitas 45, 109-118.
del Carmen, et al, (Aug. 1, 2003), "Racial Differences in Mammographic Breast Density," del Carmen, et al, Cancer, vol. 98, No. 3, 590-596.
C.A. Gateley, et al, (Oct. 1990), "Mastalgia refractory to drug treatment," C. A. Gateley, et al, British Journal of Surgery, vol. 77; 1110-1112.
J. Brooke Barham, et al, (Mar. 2000), "Addition of Eicosapentaenoic Acid to y-Linolenic Acid-Supplemented Diets Prevents Serum Arachidonic Acid Accumulation in Humans," Human Nutrition and Metabolism, 1925-1931.
Antueno, et al, (2001), "Activity and mRNA Abundance of Δ-5 and Δ-6 fatty acid desatirases om two human cell lines," FEBS Letters, 491, 247-251.
"Life-course body size and perimenopausal memmographic parenchymal patterns in the MRC 1946 British birth cohort," British Journal of Cancer (2003) 89, 852-859.
Toni Hudson, M.D., (May 2001), "Fibrocystic Breasts: A Natural Approach," Natural Pharmacy, pp. 10-12.
Susan L. Norwood, (Mar./Apr. 1990), "Fibrocystic Breast Disease, an Update and Review," JOGNN 19:2, 116-121.
Straif, et al, (2000), "Glutathione peroxidase-1 but not -4 is involved in the regulation of cellular 5-lipoxygenase activity in monocytic cells," Biochem. J., 349, 455-461.
Heine, et al, (2002), "Mammographic Tissue, Breast Cancer Risk, Serial Image Analysis, and Digital Mammography," Acad Radiol: 9:298-316.
Jiang, et al, (2003), "Levels of expression of lipoxygenases and cyclooxygenase-2 in human breast cancer," Prostaglandins, Leukotriences and Essential Fatty Acids 69, 275-281.
"The clinical assessment of mastalgia," Mansel, The British Journal of Clinical Practice, Supplement 68, pp. 17-25, dated Nov. 1989.
"Selenium," NIH Clinical Center, www.cc.nih.gov/ccc/supplements/selen.html, Dec. 8, 2003.
Blommers, et al, (Nov. 2002), "Evening primrose oil and fish oil for severe chronic mastalgia: A randomized, double-blind, controlled trial," Am. J. Obstet Gynecol, 1389-1394.
Wendy Maddocks, (2002), "Cyclical Mastalfia: Could Essential Oils Help This Condition?," Internation Journal of Aromatherapy, vol. 2, No. 1.
Millet, et al, (2002), "Clinical Management of Breast Pain: A Review, Obstetrical and Cynecological Survey," vol. 57, No. 7, 451-461.
Norlock, (2002), "Benign Breast Pain in Women: A Practice Approach to Evaluation and Treatment," JAMWA, vol. 57, No. 2, 85-90.
Hudson, (Jun. 2001), "Evening Primrose Oil in Natural Medicine," Alternative & Complementary Therapies, pp. 144-148.
Homer, et al, (Nov. 2000), "Potential mechanisms of diet therapy for fibrocystic breast conditions show inadequate evidence of effectiveness," J. Amer. Diet. Assoc., vol. 100, No. 11, 1368-1380.
Kenny, et al, (2000), "Gamma Linolenic Acid with Tamoxifen as Primary Therapy in Breast Cancer," Int. J. Cancer; 85, 643-648.
K. L. Cheung, (1999), "Management of Cyclical Mastalgia in Oriental Women: Pioneer Experience of Using Gamolenic Acid (Efemast®)," Aust. N.Z. J. Surg., 69, 492-494.
Ader, et al, (1999), "Cyclical mastalgia: premenstrual syndrome or recurrent pain disorder?" J. Psychosom. Obstet. Gynecol, 20:198-202.
Smyth, P.P., (1997), "The thyroid and breast cancer: a significant association?", Ann. Med., 29(3): 189-191.
Venturi, S. et al. (2000) "Role of iodine in the evolution and carcinogenesis of thyroid, breast, and stomach", Adv. Clin. Path., 4(1): 11-17.
Cann, S. A. et al. (2000) "Hypothesis: iodine, selenium, and the development of breast cancer", Cancer Causes Control, 11(2): 121-127.
Strum, J.M. (1978) Site of iodination in the rat mammary gland, Anat. Rec., 192:235-244.
Strum, J.M. et al (1983) "Resting human female breast tissue produces iodinated proteins", J. Ultrastruc. Res., 84:130-139.
Haagensen, C.D. (1971) "The Normal Physiology of the Breast", Diseases of the Breast, W.B. Saunders, Philadelphia, PA, p. 62.
Ghent, W.R. et al (1993) "Iodine replacement in fibrocystic disease of the breast", Can. J. Surg., 36:453-460.
Lang, W.R. et al, (1972) "Benign mammary dysplasia", Med. J. Aust., 2:147-149.
Goodwin, P.J. et al. (1998) "Elevated high-density lipoprotein cholesterol and dietary fat intake in women with cyclic mastopathy", Am. J. Obstet. Gynecol., 179:430-437.
Hollowell, J.G. et al, (1998) "Iodine nutrition in the United States: Trends and public health implications: Iodine excretion data from NHANES III", J. Clin. Endocrinol. Metab., 83(10):3401-3408.
Vitti, P. et al (2003) "Europe is iodine deficient", Lancet, 361:1226.
Jackson, M.J. et al, (2003) Marginal dietary selenium intakes in the U.K.: Are there functional consequences?, J. Nutr., 133:1557S-1559S.
Schrauzer, G.N. et al, (1985), "Selenium in the Blood of Japanese and American Women With and Without Breast Cancer and Fibrocystic Disease." Jpn. J. Can. Res.,76(5):374-377.
Tominaga, S. et al. (1997) "An ecological study on diet, nutrition and cancer in Japan", Int. J. Cancer, 10 (Suppl.):2-6.
Boeynaems, J.M., et al. (1980) "Transformation of arachidonic acid into an iodolactone by rat thyroid", J. Biol. Chem., 255 (19):9001-9004.
Cann, S.A. et al. (1999) "Iodine accumulation in extrathyroidal tissues", J. Clin. Endocrinol. Metab., 84(2): 821.
Peters, F. et al. (1985) "Thyroid hormones in benign breast disease", Cancer, 56:1082-1085.
Estes, N.C. (1981) "Mastodynoia due to fibrocystic disease of the breast controlled with thyroid hormone", Am. J. Surg., 142:764-766.
Russo, J. and Russo, I.H. (1997) "Role of differentiation in the pathogenesis and prevention of breast cancer", Endo. Rel. Cancer., 4:7-21.
Gravelle, I.H. et al. (1991) "A comparison of mammographic parenchymal patterns in premenopausal Japanese and British women", Breast Cancer Res. Treat., 18 (Supl.): 93-95.
Rayman, M.P. et al. (2003) "Low selenium status is associated with the occurrence of preeclampsia in women from the United Kingdom", Am. J. Obstet. Gynecol., 189:1343-1349.
Hotz, C.S. et al. (1997) "Dietary iodine and selenium interact to affect thyroid hormone metabolism in rats", J. Nutr., 127(6):1214-1218.
Homer, N.K. et al. (2000) "Potential mechanisms of diet therapy for fibrocystic breast disease show inadequate evidence of effectiveness", J. Am. Diet. Assoc., 100:1368-1380.
Gateley, C.A. et al. (1992) "Plasma fatty acid profiles in benign breast disorders", Br. J. Surg., 79(5):407-409.
Martinez, L. et al. (1994) "Intracystic lipidic profile in fibrocystic breast disease", Gynceol. Endocrinol., 8(4):287-292.
Eskin, B.A. (1970) "Iodine metabolism and breast cancer", Trans. N.Y. Acad. Sci., 11:911-947.

(56) References Cited

OTHER PUBLICATIONS

Eskin, B.A. et al. (1995) "Different tissue responses for iodine and iodide in rat thyroid and mammary gland", Biol. Trace Elem. Res., 49:9-19.
Strum, J.M. (1979) "Effect of iodide deficiency on rat mammary glan", Virchows Arch. [B], 30:209-220.
Vishnyakova, V.V., et al. (1966) "On the treatment of dyshormonal hyperplasia of mammary glands", Vestn. Akad. Med. Nauk SSSR, 21:19-22.
Wright, J.V. (Jul. 1995) "Fibrocystic Breasts", in Nutrition and Healing, vol. 2, No. 7.
K. Dedyna, (Sep. 9, 1997) "Iodine:Bosom buddy", reported in The Times Colonist, p. D1.
L.J. deGroot, "Graves Disease: Diagnosis and Management", in the Thyroid and its Diseases, Chapter 11 (www.thyroidmanager.org), dated 1996.
Thrall, K.D. et al. (1992) "Distribution of iodine into blood components of the Sprague-Dawley rat differs with the chemical form administered", J. Tox. Environ. Health, 37:443-449.
Boyd, N.F. et al, (1988) "Effect of a low-fat high-carbohydrate diet on symptoms of cyclical mastalgia", Lancet, 332(8603):128-132.
Shultz, T.D. et al. (1988) "Effect of high-fat intake on lactogenic hormone bioactivity in premenopausal women", Am. J. Clin. Nutr., 48:791-794.
Cheung, K.L. (1999) "Management of cyclic mastalgia in Oriental women: Pioneer experience of using GLA (Efamast) in Asia", Aust. N.Z.J. Surg., 69:492-494.
Mansel, R.E. (1995) "Breast pain", in ABC of Breast Disease (Dixon, J.M., Ed.) pp. 11-13.
Pye, J.K. et al. (1985) "Clinical experience of drug treatments for mastalgia", Lancet, 2(8451):373-377.
Gateley, C.A. et al. (1994) "Drug Therapy of Mastalgia: What are the options?", Drugs 48(5): 709-716.
MeReC Bulletin (vol. 9, No. 2; 1998) "Atopic eczema and mastalgia: the place of evening primrose oil", National Prescribing Center of the National Health Service, U.K.
Lark, Susan M. "Fibrocystic breast disease" )excerpted from the Women's Health Companion), www.healthy.net, from The Women's Health Companion (1996).
Goodwin, P.J. et al. (1988) "Cyclic mastopathy: a critical review of therapy", Br. J. Surg., 75:837-844.
Preece, P.E. et al. (1982) "Evening primrose oil (Efamast) for mastalgia", in Clinical Uses of Essential Fatty Acids, (Horrobin, D.F., ed), Eden Press, Montreal; pp. 147-154.
Wetzig, N.R. (1994) "Mastalgia: A 3-year Australian study", Aust. N.Z. J. Surg., 64(5):329-331.
Blommers, J. et al. (2002) "Evening primrose oil and fish oil for severe chronic mastalgia: A randomized, double-blind, controlled trial", Am. J. Obstet. Gynecol., 187:1389-1394.
Norlock, F.E. (2002) "Benign breast pain in women: A practical approach to evaluation and treatment", J. Am. Med. Women's Assoc., 57:85-90.
Faiz, O. et al. (2000) "Management of breast pain", Int. J. Clin. Pract., 54(4):228-232.
Marchant, D.J. (2002) "Benign breast disease", In Obstet. Gynecol. Clinics, vol. 29, No. 1 (W.B. Saunders Company).
Mayo Clinic Health Letter, "Breast pain", Apr. 2000 (www.mayoclinic.com/invoke.cfm?id).
Padden, D.L. (2000) "Mastalgia: Evaluation and management", Nurse Pract. Forum, 11(4):213-218.
Ader, D.N. et al. (1997) "Prevalence and impact of cyclic mastalgia in the United States clinic-based sample", Am. J. Obstet. Gynecol., 177(1):126-132.
Ader, D.N. et al, (1997) "Cyclic mastalgia: prevalence and impact in an outpatient breast clinic sample", J. Am. Coll. Surg., 185:466-470.
Horrobin, D.F. et al. (1989) "Premenstrual breast pain (cyclic mastalgia): Disorders of essential fatty acid (EFA) metabolism", Prostaglandins Leukot. Essent. Fatty Acids, 37:255-261.

Mansel, R.E. et al. (1990) "Effect of essential fatty acids on cyclic mastalgia and non-cyclic breast disorders", In Omega-6 Essential Fatty Acids: Pathophysiology and Roles in Clinical Medicine, (Alan R. Liss, Inc.), pp. 557-566.
Konno, N. et al. (1994) "Association between dietary iodine intake and prevalence of subclinical hypothyroidism in the coastal regions of Japan", J. Clin. Endocrinol. Metabol., 78(2):393-397.
Konno, N. et al. (1993) "Clinical evaluation of the iodine/creatinine ration of casual urine samples as an index of daily iodide excretion in a population study", Endocrin. J. 40:163-169.
Kleijnen, J. (1994) "Evening primrose oil", Br. Med. J., 309:824-825.
Phinney, A. (1994) "Potential risk of prolonged gamma-linolenic acid use", Ann. Intern. Med., 120:692.
Rayman, M.P. (2000 "The importance of selenium in human health", Lancet, 356:233-241.
Stoice, A. et al. (2000) "Effects of selenite on estrogen receptor-alpha expression and activity in MCF-7 breast cancer cells", J. Cell. Biochem., 79:282-292.
Fan, Y-Y et al. (1998) "Importance of dietary gamma-linolenic acid in human health and nutrition", J. Nutr., 128:1411-1414.
Dogliotti, L. et al. (1985) "Prolactin and thyrotropin response to TRH in premenopausal women with fibrocystic breast disease", Horm. Res., 21(3):137-144.
Zych, F. et al. (1996) "Fibrocystic disease of the breast and pituitary-thyroid axis function", Pol. Merkuriusz. Lek., 1(4):227-228.
Kumar, S. et al. (1984) "Prolactin response to TRH stimulation and dopaminergic inhibition in benign breast disease", Cancer, 53(6):1311-1315.
Gardner, D.F. et al. (1999) "Effects of low-dose oral iodide supplementation of thyroid function in normal men", Clin. Endocrinol., 28(3):283-288.
Wypych, K. et al. (2002) "Hormonal abnormalities in women with beast cysts", Ginekol. Pol., 73(11):1117-1125.
Anderson, E. et al. (1998) "Estrogen responsiveness and control of normal human breast proliferation", J. Mamm. Gland Biol. Neoplasia, 3(1):23-35.
Slebodzinski, A.B. et al. (1999) "Presence of thyroxine deiodinases in the mammary gland", Domest. Anim. Endocrinol., 17(2/3):161-169.
Martinez, L. et al. (1995) "Thyroid hormones in fibrocystic breast disease", Eur. J. Endocrinol., 132(6):673-676.
Hochberg. R.B. (1998) "Biological esterification of steroids", Endocrine Reviews, 19(3):331-348.
Strott, C.A. (2002) "Sulfonation and molecular action", Endocrine Reviews, 23(5):703-732.
Pierce, P.K. (2002) "Cyclic mastalgia: primary care management", Clin. Excel. Nurse. Pract., 6(3):45-48.
Khanna, A.K. et al. (2002) "Behaviour of estrogen receptor, histological correlation, and clinical outcome in patients with benign breast disease", Eur. J. Surg., 168:631-634.
Horrobin, D.F. (1983) "The role of essential fatty acids and prostaglandins in the premenstrual syndrome", J. Reprod. Med., 28(7):465-468.
Johnson, M.M. et al (1997) "Dietary supplementation with GLA alters fatty acid content and eicosanoid production in healthy humans", J. Nutr. 127:1435-1444.
Dugrillon, A. (1996) "Iodolactones and iodoaldehydes: mediators of iodine in thyroid regulation", Exp. Clin. Endocrinol. Diabetes, 104(Suppl. 4):41-45.
Gartner, R. et al. (1996) "Evidence that iodolactones are the mediators of growth inhibition by iodine on the thyroid", Acta Med. Austriaca, 23(1/2):47-51.
Langer, R. et al. (1996) "Influence of iodide and iodolactones on thyroid apoptosis:evidence that apoptosis induced by iodide is mediated by iodolactones in intact porcine thyroid follicles", Exp. Clin. Endocrinol. Diabetes, 111(6):325-329.
Turk, J. et al. (1983) "Iodination of arachidonic acid mediated by eosinophilic peroxidase, myeloperoxidase, and lactoperoxidase: identification and comparison of products", Biochim. Biophys. Acta, 751(2):189-200.
Lubin, f. et al. (1989) "Nutritional factors associated with benign breast disease etiology: a case-control study", Am. J. Clin. Nutr., 50:551-556.

(56) References Cited

OTHER PUBLICATIONS

Hunter, D.J. et al. (1997) "Non-dietary factors as risk factors for breast cancer and as effect modifiers of the association of fat intake and risk of breast cancer", Cancer Causes Control, 8:49-56.

Dorgan, J.F. et al (1996) "Relation of energy, fat, and fiber intakes to plasma concentrations of estrogens and androgens in premenopausal women", Am. J. Clin. Nutr. 64:24-31.

Baer, H.J. et al. (2003) "Adolescent diet and incidence of proliferative benign breast disease", Can. Epidemiol. Biomark. Prevent., 12:1159-1167.

Lamer, J.M. et al. (1985) "Synthesis of estradiol fatty acid esters by human breast tumors: fatty acid composition and comparison to estrogen and progesterone receptor content", J. Steroid Biochem., 23(5A):637-641.

Lamer, J.M. et al (1992) "Measurement of estradiol-17-fatty acid esters in human tissues", J. Clin. Endrocrinol. Metab., 75(1):195-200.

Kothari, M. (2003) "Benign breast disorders", Chemist & Druggest, Mar. 1): 19-22.

Boyd, N.F. et al. (1997) "Effects at two years of a low-fat high-carbohydrate diet on radiologic features of the breast: results from a randomized trial", J. Natl. Cancer Inst., 89:488-496.

Boccardo, F. et al. (2003) "Enterolactone in breast cyst fluid: correlation with EGF and breast cancer risk", Breast Can. Res. Treat., 79(1):17-23.

Tyers, N.M. et al. (1995) "Altered oestrogen receptor expression in human breast cells following exposure to evening primrose oil", J. Pharm. Pharmacol., 47:1087.

Kenny, F. S. et al. (2000) "Gamma linoleic acid with tamoxifen as primary therapy in breast cancer", Int. J. Cancer, 85(5):643-648.

Kenny, F.S. et al. (2001) "Effect of dietary GLA +/- tamoxifen on the growth, ER expression, and fatty acid profile of ER-positive human breast cancer xenografts", Int. J. Cancer, 92(3):342-347.

Ha, E.J. and Smith, A.M. (2003) "Plasma selenium and plasma and erythrocyte glutathione peroxidase activity increase with estrogen during the mentrual cycle", J. Am. Coll. Nutr., 22(1):43-51.

El-Bayoumy, K. (1994) "Evaluation of chemopreventive agents against breast cancer and proposed strategies for future clinical intervention trials", Carcinogenesis, 15:2395-2420.

Hu, J.H. and Diamond, A.M. (2003) "Role of glutathione peroxidase 1 in breast cancer: loss of heterozygosity and allelic differences in the response to selenium", Cancer Res., 63:3347-3351.

Russo, J. et al. (2001) "Carcinogenicity of estrogens in human breast epithelial cells", Acta Pathol. Microbial. Immunol. Scand., 109:39-52.

Hawkes, W.C. et al. (2003) "Dietary selenium intake modulates thyroid hormone and energy metabolism in men", J. Nutr., 133(11):3443-3448.

Kohrle, J. (1999) "Local activation and inactivation of thyroid hormones: the deiodinase family", Mol. Cell. Endocrinol., 151:103-119.

Garcia-Solis, P. and Aceves, C. (2003) "5'-deiodinase in two breast cancer cell lines: effect of T3, isoproterenol, and retinoids", Mol. Cell. Endocrinol., 201(1-2):25-31.

Song, W.C. (2001) "Biochemistry and reproductive endocrinology of estrogen sulfotransferase", Ann. N.Y. Acad. Sci., 948:43-50.

Suzuki, T. et al. (2003) "Estrogen sulfotransferase and steroid sulfatase in human breast carcinoma", Cancer Res., 63:2762-2770.

Rubin, G.L. et al. (1999) "Regulation of sulfotransferase expression in the endometrium in the menstrual cycle, by oral contraceptives, and during early pregnancy", Mol. Human Reprod., 5:995-1002.

Miki, Y. et al. (2002) "systemic distribution of steroid sulfatase and estrogen sulfotransferase in human adult and fetal tissues", J. Clin. Endocrinol. Metab., 87(12):5670-5768.

Qian, Y.M. et al. (2001) "Targeted disruption of the mouse EST gene reveals a roel of estrogen metabolism in intracrine and paracrine estrogen regulation", Endocrinol., 142(12):5342-5350.

Werz, O. (2002) "5-lipoxygenase: cellular biology and molecular pharmacology", Curr. Drugs Inflamm. Allergy, 1(1):23-44.

Strait, D. et al. (2000) "Glutathione peroxidase-1 but not -4 is involved in the regulation of cellular 5-lipoxygenase activity in monocytic cells", Biochem. J., 349(Pt. 2):455-461.

Gartner, R. et al. (2002) "Selenium supplementation in patients with autoimmune thyroiditis decreases thyroid peroxidase antibodies concentration", J. Clin. Endocrinol., Metab., 87:1687-1691.

Peretz, A. et al. (1992) "Adjuvant treatment of recent onset rheumatoid arthritis by selenium supplementation", Br. J. Rheumatol., 31:281-286.

Stadel, B.V. (1976) "Dietary iodine and risk of breast, endometrial, and ovarian cancer", Lancet, 1:890.

Siiteri, P.K. et al. (1981) "Increased availability of serum oestrogens in breast cancer: a new hypothesis", in Hormones and Breast Cancer (Banbury Report #8, Cold Spring Harbor Laboratories), pp. 87-101.

Tanosaki, S. et al. (2003) "Effect of ligands of nuclear hormone receptors on sodium/iodide symporter expression and activity in breast cancer cells", Breast Cancer Res. Treat., 79(3):335-345.

Jiang, W.G. et al (2000) "Peroxisome proliferator activated receptor-gamma, ediates the action of gammalinolenic acid in breast cancer cells", Prostaglandins Leuko. Essent. Fatty Acids, 62(2):199-127.

Corton, C.J. et al. (2000) "Central role of PPARs in the actions of peroxisome proliferators", Ann. Rev. Pharmacol. Toxicol., 40:491-518.

Flaxseed Supplementation Positively Influences Bone Metabolism in Postmenopausal Women, Bahran J. Arjmandi, et al, vol. 1, No. 2 JANA 27, Fall 1998.

Soy Protein and Isoflavones: Their effects on blood lipids and bone density in postmenopausal women, Susan M Potter, et al, Am J Clin Nutr, 1998; 68(suppl): 1375S-9S.

Soybean Isoflavones Dose-Dependently Reduce Bone Turnover but Do Not Reverse Established Osteopenia in Adult Overiectomized Rats, Picherit, et al, J. Nutr. 131: 723-728, 2001.

Role of Soy Protein with Normal or Reduced Isoflavone Content in Reversing Bone Loss Induced by Ovarian Hormone Deficiency in Rats, Arjmandi, et al, Am. J Clin. Nutr. 1998;68 (suppl): 1358S-63S.

Prunes Test Highest in Important Health-Sustaining Compounds, Plum Good News, vol. XI, The California Prune Board, dated Apr. 1999.

Dried Plums Create the Perfectly Balanced Energy Bar: Perfect Nutrition . . . Perfect Taste and Texture, California Prune Board Food Technology, Technical Bulletin, dated May 1999.

Various Selected Vegetables, Fruits, Mushrooms and Red Wine Residue Inhibit Bone Resorption in Rats, Roman C. Muhlbauer, et al, J. Nutr. 133: 3592-3597, 2003.

True Calcium Absorption in the Intestine is Enhanced by Fructooligosaccharide Feeding in Rats, Tomio Morohashi et al, J. Nutr. 128: 1815-1818, 1998.

Effect of Acetate and Propionate on Calcium Absorption from the Rectum and Distal Colon of Humans, Trinidad P Trinidad, et al, Am. J. Clin Nutr 1996;63:574-8.

Nondigestible oligosaccharides do not interfere with calcium and nonheme-iron absorption in young, healthy men, Ellen GHM van den Heuvel, et al, Am J Clin Nutr 1998;67:445-51.

Prune: Its Efficacy in Prevention of Ovarian Hormone Deficiency-Induced Bone Loss, B.H. Arjmandi, et al, (SU334 Abstract), S515, (1999).

Prune Dose-Dependently Reverses Bone Loss in Ovarian Hormone Deficient Rats, F. Deyhim, et al, (SA344 Abstract) S394, (1999).

Dietary Fructooligosaccharides Improve Soy-Osteopenia Prevention in the Ovariectomized Rat, J. Mathey et al, (SU358 Abstract), (2003).

Effects of Soy, Fructooligosaccharide, and their Combination on Reversal of Bone Loss in Ovariectomized Osteopenic Rats, L.J. Hammond, et al, (SU364 Abstract), accessed May 2004.

Flaxseed Improves Lipid Profile without Altering Biomarkers of Bone Metabolism in Postmenopausal Women, Edralin A. Lucas, et al, J Clin Endocrinol Metab 87: 1527-1532, 2002.

Exposure to purified lignan from flaxseed (*Linum usitatissimum*) alters bone development in female rats, Wendy E. Ward, et al, British Journal of Nutrition (2001), 86, 499-505.

Early exposure to flaxseed or its purified lignan affects the femur properties of female but not male rats, W. E. Ward, et al, Abstract 163.6 from Nutrients and Bone Mineral Metabolism A224, Apr. 15-18, 2000.

(56) References Cited

OTHER PUBLICATIONS

A Combination of Dietary Fructooligosaccharides and Isoflavone Conjugates Increases Femoral Bone Mineral Density and Equol Production in Ovariectomized Mice, Atsutane Ohta, et al, J. Nutr. 132: 2048-2054, 2002.
Dried Plums Improve Indices of Bone Formation in Postmenopausal Women, Bahram H. Arjmandi, et al, J of Women's Health & Gender—Based Medicine, vol. 11, No. 1, 2002.
Chemical Composition and Potential Health Effects of Prunes: A Functional Food? Stacewicz-Sapuntzakis M, Crit. Rev Food Sci Nutr. May 2001; 41(4):251-86.
A Combination of Dietary Fructooligosaccharides and Isoflavone Conjugates Increases Femoral Bone Mineral Density and Equol Production in Ovariectomized Mice, Ohta A, et al, J Nutr. Jul. 2002;132(7):2048-54 (Abstract).
Differential Effects of Dietary Flaxseed Protein and Soy Protein on Plasma Triglyceride and Uric Acid Levels in Animal Models, Bhathena SJ, et al, J Nutr Biochem, Nov. 13, 2002(11):684-689. (Abstract).
Supplementation with Flaxseed Alters Estrogen Metabolism in Postmenopausal Women to a Greater Extent than Does Supplementation with an Equal Amount of Soy, Brooks JD, et al, Am J Clin Nutr. Feb. 2004; 79(2):318-25. (Abstract).
Combination of Soy and Sub-Optimal Dose of 17β-Estradiol May Reverse Bone Loss in a Rat Model of Postmenopausal Osteoporosis, L. Devareddy, et al, M372 Abstract, J Bone Miner Res, 18(2):S384 2003.
Dietary Fructooligosaccharides Modify Intestinal Bioavailability of a Single Dose of Genistein and Daidzein and Affect Their Urinary Excretion and Kinetics in Blood Rats, Mariko Uehara, et al, J. Nutr. 131: 787-795, 2001.
Bioavailability, Disposition, and Dose-Response Effects of Soy Isoflavones When Consumed by Healthy Women at Physiologically Typical Dietary Intakes, Kenneth D.R. Setchell, et al, J. 133: 1027-1035, 2003.
Evaluation of the Effect of Soybean Milk and Soybean Milk Peptide on Bone Metabolism in the Rat Model with Ovariectomized Osteoporosis, Naomi Omi, et al, J. Nutr. Sci. Vitaminol, 40, 201-211, 1994.
Isoflavone-rich soy protein isolate attenuates bone loss in the lumbar spine of perimenopausal women, D Lee Alekel, et al, Am J. Clin Nutr. 2000;72:844-52.
Whole Flaxseed Consumption Lowers Serum LDL-Cholesterol and Lipoprotein(a) Concentrations in Postmenopausal Women, Bahram H. Arjmandi, et al, Nutrition Research, vol. 18, No. 7 pp. 1203-1214, 1998.
Effects of Fructooligosaccharides on Bone and Mineral Absorption in the Rat Model with Ovariectomized Osteoporosis, Azusa Taguchi, et al, Nov. 1, 1994.
Dietary Soybean Protein Prevents Bone Loss in an Ovariectomized Rat Model of Osteoporosis, Bahram H. Arjmandi, et al, J. Nutr. 126: 161-167, 1996.
Oligofructose Stimulates Calcium Absorption in Adolescents, Ellen GHM van den Heuvel, et al, Am. J. Clin. Nutr., 1999; 69:544-8.
Fructooligosaccharide Consumption Enhances Femoral Bone Volume and Mineral Concentrations in Rats, Sawa Takahara, et al, J. Nutr. 130: 1792-1795, 2000.
A Randomized Study on the Effects of Estrogen/Gestagen or High Dose Oral Calcium on Trabecular Bone Remodeling in Postmenopausal Osteoporosis, T. Steiniche, et al, Bone, 10, 313-320 (1989).
Raloxifene Inhibits Bone Turnover and Prevents Further Cancellous Bone Loss in Adult Ovariectomized Rats with Established Osteopenia, Glenda L. Evans, et al, Endocrinology, vol. 137, No. 10, 4139-4144, 1996.
[P-44] Abstract #97.061, Soy Phytoestrogens and Bone, Pansini F, et al, NAMS, 1997.
Notice of Allowance in Canadian Application No. 2,564,592 dated Oct. 1, 2012.

* cited by examiner

COMPOSITIONS FOR IMPROVING BREAST HEALTH IN WOMEN

This application is related to Provisional Application No. 60/566,625 filed Apr. 29, 2004 and Provisional Application No. 60/629,789 filed Nov. 19, 2004.

The present invention relates to compositions containing select combinations of gamma linolenic acid (GLA), iodine, and preferably selenium, for improving breast health in women.

BACKGROUND OF THE INVENTION

Among the most common health issues affecting women today is that of breast health, most notable of which includes fibrocystic breast disease or related fibrotic conditions, premenstrual or cyclic breast pain and tenderness, breast cancer, elevated or excessive mammographic breast density, and even unexplained breast pain and tenderness without clear association with an identifiable disease or condition.

Fibrocystic breast disease is a benign condition in premenopausal women characterized by the presence of lumps and fluid-filled cysts in the breasts that may be associated with cyclic or non-cyclic pain (mastalgia) and tenderness. Fibrocystic breast conditions include atypical palpatory findings such as breast nodularity (diffuse or localized), breast thickening or swelling, tenderness, lumpiness, cysts, discrete masses, fibrosis, and pain, although breast pain may also occur in the absence of palpable lumps or cysts. A physical exam, mammography or ultrasound, biopsy of the breast, or a fine needle aspiration of larger cysts are used principally as diagnostic strategies to rule out the possibility of breast cancer or underlying malignancy.

The occurrence of fibrocystic breast disease is widespread. It is believed that almost 50% of women of child-bearing age in the United States are afflicted by and suffer from the symptoms of fibrocystic breast disease, which most commonly includes at least some degree of mastalgia or breast pain in many of these women.

Mastalgia associated with fibrocystic breast disease is often characterized as moderate to severe pain that lasts for more than about four days per month. The pain and tenderness may be either cyclic or non-cyclic, with cyclic mastalgia occurring regularly during the luteal phase of the menstrual cycle. Cyclic mastalgia associated with fibrocystic breast disease, however, is distinguishable from the cyclic pain and tenderness associated with breast swelling as a normal aspect of the premenstrual cycle, in that cyclic mastalgia associated with fibrocystic breast disease is typically more severe and lasts longer, usually from about 5 to 14 days.

It is believed that mastalgia associated with fibrocystic breast disease is caused by or somehow related to factors such as ovarian hormone changes, intake of caffeine and caffeine-containing products, excessive dietary intake of saturated fat, low intake of dietary fiber, stress, and other factors. Hormonal dysfunction, for example, may involve a progesterone deficiency in the luteal phase of the menstrual cycle, excess production of estrogen or prolactin, or a heightened sensitivity of breast tissue to the action of normal levels of circulating estrogen or prolactin. Estrogen has been found to increase fluid and sodium retention that may lead to swelling and generalized fibrocystic changes in the breasts. The role of estrogen and prolactin as central mediators of the pain and changes in breast physiology associated with fibrocystic breast disease is evidenced by the efficacy of drugs such as danazol and bromocriptine that interfere with these hormonal activities.

Current treatments for mastalgia associated with fibrocystic breast disease include dietary modifications or supplements, steroidal and non-steroidal anti-inflammatory drugs or analgesics, changes in hormone therapy (e.g., oral contraceptives), or other prescription medications. Non-steroidal anti-inflammatory drugs such as ibuprofen, naproxen, ketoprofen, and others, are commonly used in this context but often provide inadequate pain relief in many women. Hormone-based medications such as danazol (estrogen antagonist), bromocriptine (prolactin inhibitor), tamoxifen or raloxifene (partial estrogen antagonist) are also prescribed for women afflicted with fibrocystic breast disease but moderate to severe side effects limits its use in many women, especially when these hormone-based medications are continued over long periods of time.

Still other known or suggested treatments for treating fibrocystic breast disease include the use of various nutrients or supplements, some of which include vitamin E, evening primrose oil or borage oil with gamma linolenic acid (GLA), vitamin $B_6$, thiamine, iodine, and vitamin A.

Many of these treatments, however, have been met with only limited success. Iodine, for example, is often limited by its potential for dose-related toxicity, especially at those doses believed to be most therapeutic for treating fibrocystic breast disease symptoms. Due in part to toxicity concerns, iodine is less often used in fibrocystic breast disease than other nutrients such as GLA, a polyunsaturated fatty acid that has likewise shown promise in treating fibrocystic breast disease symptoms. GLA has been found to be effective in treating fibrocystic breast disease while causing few if any serious side effects. Although GLA has been shown to be somewhat effective in treating fibrocystic breast disease, it is often limited in use by its eggy, chicken fat, sulfidy off-flavor, as well as the large number capsules often needed to provide a therapeutic daily dose.

Moreover, many women suffer from various breast-related health issues other than or in addition to fibrocystic breast disease. These other conditions include premenstrual or cyclic breast pain and tenderness, the development of breast cancer or other estrogen-sensitive cancers, elevated or excessive mammographic breast density with or without associated fibrocystic breast disease, and even unexplained breast pain and tenderness without any clear association of an identifiable disease or condition. Common to all such breast-related issues is that no single treatment method provides complete relief from symptoms in all women without any significant side effects.

There is, however, substantial overlap among the different treatments for fibrocystic breast disease as discussed above and the treatments for other breast related-diseases or conditions. Analgesics, for example, are often prescribed for many of these other breast-related conditions, most notable of which includes the breast pain and tenderness associated with premenstrual cycles. As with treatments for fibrocystic breast disease, there remains for other breast-related diseases or conditions a need for alternative treatments that potentially help more women, provide improved relief from symptoms, and enhance the quality of life in women who have historically suffered for lack of sufficient treatments.

It is therefore an object of the present invention to provide an alternative treatment for women afflicted with fibrocystic breast disease and other breast-related diseases or conditions, and further to provide a treatment that is highly effective in reducing associated breast pain and tenderness, reducing mammographic breast density, reducing the rate or risk of undesirable cell proliferation in breast tissue, or combinations thereof.

It is a further object of the present invention to provide such a treatment that is well tolerated by individuals, and further to provide such a treatment this is potentially even more effective in reducing breast pain and tenderness than currently available treatments. It is further object of the present invention to provide such a treatment through the daily oral administration of a well-tolerated, highly effective, nutritional product.

It is a further object of the present invention to provide a nutritional composition or medical food that can be taken as a single, daily, nutritional product by women afflicted with fibrocystic breast disease or other breast-related diseases or conditions, which combines the therapeutic benefits of iodine, GLA, and optional selenium, in a product form that provides for improved patient compliance, improved oral tolerance, improved relief from breast pain and tenderness, reduction in mammographic breast density, reduction in the rate or risk of undesirable cell proliferation in breast tissue, fewer or less severe side effects, or combinations thereof.

These and other objects of the present invention are described and shall be apparent from the description as set forth hereinafter.

SUMMARY OF THE INVENTION

The present invention is directed to oral compositions for treating fibrocystic breast disease or other breast-related diseases or conditions, wherein the compositions comprise from zero to about 400 μg selenium, from about 100 mg to about 6000 mg gamma linolenic acid, and from about 0.15 mg to about 5.0 mg iodine. The present invention includes nutritional embodiments further comprising one or more nutrients such as protein, lipid, carbohydrates, minerals, and vitamins.

The present invention is also directed to methods of using the oral compositions of the present invention in women afflicted with fibrocystic breast disease or other breast-related diseases or conditions, some of which are directed to 1) reduction in mammographic breast density, 2) reduction in the risk of developing breast cancer, 3) reduction in mammary tumor cell proliferation and invasion (metastasis) associated with the development, progression, and/or recurrence of breast cancer and/or the progression of fibrocystic breast disease, and/or 4) treatment or reduction of symptoms associated with this disease, including treatment of breast tenderness and pain, and combinations thereof.

The compositions of the present invention provide effective relief from the symptoms of fibrocystic breast disease or other breast-related diseases or conditions in a larger percentage of women as compared to many other nutrient-based therapies. It is believed that the combination of key active ingredients, each of which has a different mechanism of action when used in breast-related diseases and conditions, provides for a more effective product or therapeutic treatment in a larger percentage of women.

The compositions of the present invention may also be better tolerated and result in improved patient compliance. These compositions are most typically administered as a single, undivided, serving, e.g., nutritional liquid or solid product form, which is easily taken by an individual once daily, without concern for taking many different tablets or capsules or medicated solutions containing the different actives or for measuring out potassium iodide solutions every morning.

It has now been found that certain combinations of selenium, iodine, and GLA are surprisingly more effective than individual actives when evaluated for in-vitro activity in reinforcing the function of tight junctions of endothelial cells and on mammary epithelial cells. Damage to the cell-cell adhesion and tight junction in the epithelium or endothelium by any means (e.g. estrogen) may result in an increase to the permeability of cell layer to fluids and micro/macro-molecules. This can then lead to edema and swelling of tissues, followed by mastalgia. In fact applicants discovered that these combinations of actives are especially effective in this regard when used on test cells in the presence of estrogen. This data suggests that the various active combinations would be especially effective and useful in nutritional or other formulations to help treat symptoms of estrogen-sensitive fibrocystic breast disease or other estrogen-sensitive breast-related disease or condition, including cyclical breast pain or mastalgia (see Experiment I, FIGS. 1-10)

It has also been found, based upon in-vitro data described hereinafter, that GLA, iodine and selenium may control or limit proliferation of fibrocystic and breast cancer cells, and thus reduce the risk of proliferative conditions or diseases such as fibrocystic breast disease, breast cancer, and increased breast density (Experiment II, FIGS. 11-16).

It has also been found, based upon in-vitro data described hereinafter, that various combinations of GLA, iodine, and selenium may inhibit vascular invasion of endothelial cells by breast cancer cells, thus reducing the potential risk of cancer metastasis, especially in those individuals at risk of recurrence of highly invasive cancer types. The data shows that the specific combination of selenium, iodine, and GLA was most effective in this respect, showing a dramatic result relative to the control (Experiment II, FIG. 10)

DETAILED DESCRIPTION OF THE INVENTION

Figure 1:
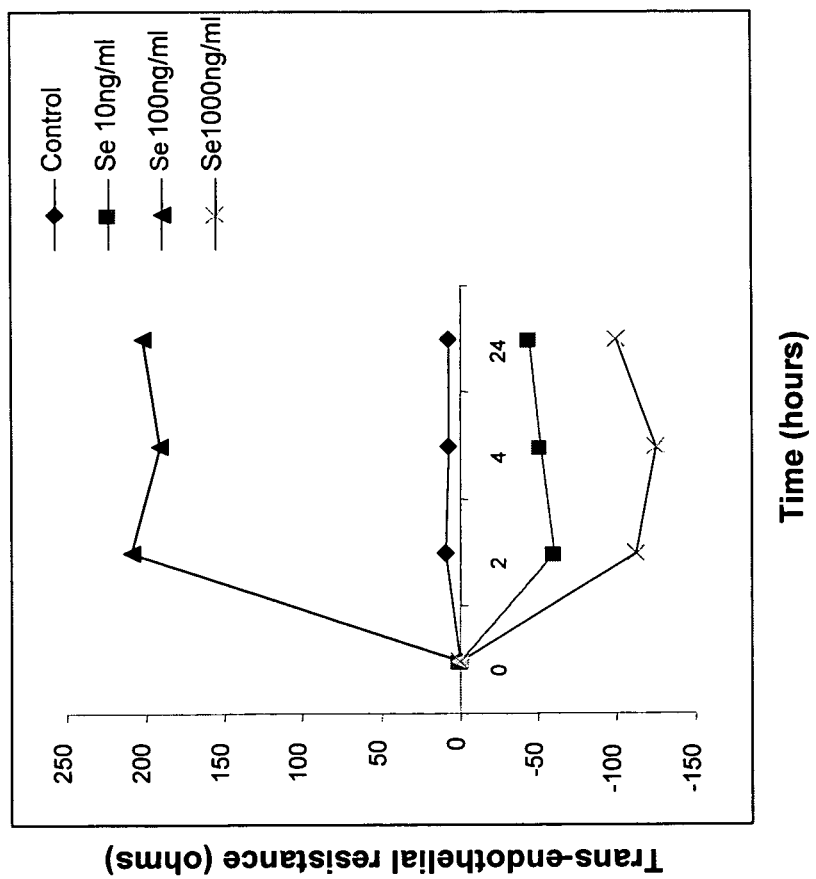
FIG. 1 is a graph of trans-endothilial resistance (ohms) over 24 hours for human endothelial cells (HECV) treated with selenium at 10 ng/ml, 100 ng/ml, and 1000 ng/ml, or untreated (control).

The compositions and corresponding methods of the present invention are directed to nutritional and pharmaceutical products, including medical foods, containing gamma linolenic acid, iodine, and preferably selenium, for use in women afflicted with fibrocystic breast disease or other breast related disease or condition. These and other essential or optional elements or limitations of the compositions and methods of the present invention are described in detail hereinafter.

The terms "treating" or "treat" as used herein, unless otherwise specified, include controlling, preventing, or otherwise reducing the occurrence, severity or relapse of an identified symptom, condition, or disease, in individuals afflicted with or prone to develop such symptoms, condition or disease.

The terms "fibrocystic breast disease" as used herein, and unless otherwise specified, includes diffuse cystic mastopathy, cystic breast, mammary dysplasia, cystic mastitis, cystic mastopathy, cyclic mastalgia, benign breast disease, lumpy breast, diffuse cyclic mastopathy, and chronic cystic mastitis, all of which are different terms often used in the literature to generally refer to the same or similar benign condition described herein as fibrocystic breast disease.

The phrase "breast-related disease or condition" as used herein, and unless otherwise specified, includes conditions, diseases, or symptoms thereof, which may or may not occur in the presence of fibrocystic breast disease, examples of which include premenstrual breast pain or tenderness (i.e., premenstrual syndrome), cyclic or non-cyclic breast pain or tenderness, breast cancer, elevated mammographic breast density, and combinations thereof.

The term "lipid" as used herein, unless otherwise specified, means fats, oils, and combinations thereof, excluding the gamma linolenic acid component, which is accounted for separately in the compositions hereof.

The term "nutritional product" as used herein, unless otherwise specified, means any orally administered product containing one or more macronutrients, and having a preferred caloric content of at least about 50 kcal per daily or single serving or per individual dosage form.

The terms "serving" and "dose" are used interchangeably herein, and unless otherwise specified, refers to the amount of a composition of the present invention to be administered to an individual at one time. In this context, a serving or dose is preferably a single dosage form, although a plurality of dosage forms can also be administered as a serving or dose to an individual at one time. For nutritional embodiments of the present invention, a serving or dose is further defined by a caloric content of at least about 50 kcal, preferably from about 50 kcal to about 1000 kcal.

The term "medical food:" as used herein, unless otherwise specified, refers generally to food that is formulated to be consumed or administered enterally under the supervision of a physician and that is intended for the specific dietary management of a disease or condition for which distinctive nutritional requirements, based on recognized scientific principles, are established by medical evaluation.

The term "mastalgia" as used herein, unless otherwise specified, refers to breast pain, breast tenderness, or combinations thereof.

The term "pharmaceutical composition" as used herein, unless otherwise specified, refers to any oral composition that is not a "nutritional composition" as also defined herein. A pharmaceutical composition is therefore a composition that contains little if any added macronutrient, and can be formulated into any safe and effective oral product form such as a tablet, capsule, liquid, and so forth.

All selenium and iodine amounts, concentrations, or percentages as referenced herein are calculated as or based upon molecular selenium and molecular iodine, respectively, unless otherwise specified. For example, 100 g of potassium iodide provides 76.45 g of iodine (i.e., molecular iodine).

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

Any reference to singular characteristics or limitations of the present invention shall include the corresponding plural characteristic or limitation, and vice versa, unless otherwise specified or clearly implied to the contrary by the context in which the reference is made.

Any combination of method or process steps as used herein may be performed in any order, unless otherwise specified or clearly implied to the contrary by the context in which the referenced combination is made.

The compositions and methods of the present invention may comprise, consist of, or consist essentially of the essential elements and limitations of the invention described herein, as well as any additional or optional ingredients, components, or limitations described herein or otherwise useful in a nutritional or pharmaceutical application.

Product Form

The compositions of the present invention are directed to any known or otherwise suitable product form for oral administration. Any solid, liquid, or powder form, including combinations or variations thereof, are suitable for use herein, provided that such forms allow for safe and effective oral delivery of the essential and other selected ingredients in the targeted product form.

Non-limiting examples of solid nutritional product forms suitable for use herein include snack and meal replacement products, including those formulated as bars, sticks, cookies or breads or cakes or other baked goods, frozen liquids, candy, breakfast cereals, powders or granulated solids or other particulates, snack chips or bites, and so forth.

Non-limiting examples of liquid nutritional product forms suitable for use herein include snack and meal replacement products such as those formulated as juices or other acidified beverages, milk or soy-based beverages, shakes, coffees, teas, carbonated beverages, non-carbonated beverages, enteral feeding compositions, and so forth. These liquid compositions are most typically formulated as suspensions or emulsions, but can also be formulated in any other suitable form such as solutions, liquid gels, and so forth.

Other non-limiting examples of suitable product forms for use herein include semi-solid or semi-liquid compositions such as puddings, gels, and so forth.

The selected product form may be packaged in any known or otherwise suitable single or multi-dose package or container. It is preferred, however, that the product form be packaged as a single serving unit that is then taken daily or as otherwise directed by the individual's physician.

A single serving of the nutritional product of the present invention, whether packaged as an individual/single or multi-dose product form, comprises or provides at least about 50 kcal, preferably from about 50 kcal to about 1000 kcal, of energy per serving.

The pharmaceutical embodiments of the present invention can likewise be formulated into any known or otherwise suitable oral dosage or product form that is compatible with the selected ingredients for use in the composition and is safe for oral administration. Non-limiting examples of such oral product forms include capsules, tablets, caplets, liquids (e.g., suspensions, solutions, emulsions), powders or other particulates, and so forth. The pharmaceutical composition of the present invention may comprise a plurality of dosage forms, but preferably comprises a single dosage form containing all of the ingredients from the recited composition. When a plurality of oral dosage forms is used to contain the composition, then it is highly preferred that the plurality of dosage forms, typically that which represents a single or daily therapeutic dose, is contained, combined, or otherwise associated in a single package or dosing kit.

Selenium

The compositions of the present invention preferably comprise selenium or a suitable source of selenium, which provides the composition with from zero to about 400 µg, preferably from about 25 µg to about 400 µg of selenium, per serving or dose. The source of selenium can be any known or otherwise suitable source that is safe and effective for oral administration and is compatible with the essential and other ingredients in the selected product form.

Selenium is a trace element essential for human and animal life. It is well known that selenium influences oxidative processes in the body as well as thyroxin metabolism. In humans, selenium is predominantly taken in by dietary consumption of plants or vegetables, egg yolk, fish and meat, in particular chicken and pork, as well as by nutritional or other processed food supplements. The minimum selenium supply required for humans depends upon the chemical form of the consumed element and on the composition of the diet in which it is present. The recommended U.S. dietary allowance (RDA) for most adults is about 55 µg. The RDA for women during pregnancy and lactation is about 60 µg and 70 µg, respectively.

Although many common nutrients may be consumed in relatively large quantities without adverse health effects, ingestion of high levels of some essential nutrients such as selenium and iodine (described hereinafter) may be toxic. To maintain ordinary health, one must balance the need for a minimum amount of such compounds with the need to protect against over-ingestion to the point of toxicity. This is particularly appropriate for individuals afflicted with fibrocystic breast disease or other breast related disease or condition and who may also benefit from taking iodine as an active ingredient for associated treatment thereof.

The compositions of the present invention, in order to provide the requisite therapeutic breast-health benefits from selenium while also minimizing dose-dependent toxicity, comprise a selenium source that preferably provides from about 25 µg to about 250 µg, including from about 50 µg about 250 µg, also including from about 70 µg to about 150 µg, of selenium per serving.

The selenium source for use herein may include organic or inorganic forms of selenium, which can be provided as in isolated or pure selenium source or as part of other added ingredients such as multi-vitamins, trace mineral premixes, or other added macronutrients or ingredients, many different commercially available sources of which are well known in the various arts.

Non-limiting examples of some suitable selenium sources, organic or inorganic, include selenium oxide, selenium amino acid complex, sodium selenate, sodium selenite, L-selenomethionine, selenocysteine, selenium-rich yeast, L-Se-methylselenocysteine, and the selenium sources and premixes described in U.S. Pat. No. 5,221,545 (Borschel et al.), which description is incorporated by reference herein. The compositions of the present invention preferably contain at least about 50%, including from about 75% to 100%, by weight of the selenium as selected from the group consisting of sodium selenate, sodium selenite, selenium oxide, selenium amino acid complex, L-selenomethionine, selenium-rich yeast, and combinations thereof.

Gamma Linolenic Acid (GLA)

The compositions of the present invention comprise GLA or a suitable source of GLA, which ultimately provides the compositions with from about 100 mg to about 6000 mg of GLA, per serving or dose. The source of GLA may be any known or otherwise suitable source that is safe and effective for oral administration and is compatible with the essential and other ingredients in the selected product form.

GLA is an n-6 (omega-6) polyunsaturated fatty acid (18:3 n-6; 6,9,12-octadecatrienoic acid; (Z,Z,Z)-6,9,12-octadecatrienoic acid; cis-6, cis-9, cis-12-octadecatrienoic acid; gamolenic acid; gamma linolenic acid) well known for use in treating various skin diseases, premenstrual syndrome, diabetes, inflammatory and autoimmune disorders, cancer, fibrocystic breast disease, and so forth.

The GLA source for use in the nutritional compositions of the present invention preferably provides from about 250 mg to about 3000 mg, including from about 500 mg to about 2000 mg, also including from about 750 mg to about 1200 mg, of GLA per serving or dose. The GLA for use in the nutritional compositions may be provided as a separate, isolated or pure source of GLA or as part of other added ingredients. Sources of GLA include evening primrose oil (typically 8-14% GLA), borage oil (typically 17-25% GLA), blackcurrant seed oil (14-20% GLA), transgenic GLA sources, purified GLA (typically 26-99% GLA), fungal oils (e.g., *Mucor javanicus*), and so forth.

Borage oil is preferred as a GLA source for use in the nutritional compositions of the present invention. Borage oil has a relatively high GLA content and its specific GLA component has an advantageous stereo specificity (as attached therein to a triglyceride backbone), wherein the GLA is esterified primarily in an Sn-2 position. Other oils such as evening primrose oil and black currant oil have a GLA component esterified mainly at an Sn-3 position, and fungal oils have a GLA component esterified at both Sn-2 and Sn-3 positions. It is believed that borage oil, with its unique stereo-specific makeup and high GLA content, is more effective than other GLA-containing oils at elevating the levels of key metabolites (DGLA and 15-HETrE) that are associated with anti-inflammatory and anti-proliferative properties, both of which are helpful in treating fibrocystic breast disease and most any breast-related disease or condition.

The compositions of the present invention also preferably contain at least about 50%, including from about 75% to 100%, by weight of the gamma linolenic acid as GLA provided by an oil selected from the group consisting of borage oil, black currant seed oil, evening primrose oil, transgenic (genetically modified) vegetable oil containing at least about 20% by weight of GLA, and combinations thereof, preferably borage oil.

Moreover, it is believed that GLA is rendered more effective when administered in a nutritional or pharmaceutical composition as described herein, wherein the composition contains a combination of iodine and optional selenium at the serving concentration ranges described herein. The nutritional embodiments of the present invention are particularly useful in providing high dose administration of therapeutic GLA levels from a well-tolerated product form.

Iodine

The nutritional compositions of the present invention also comprise iodine or a suitable source of iodine, which ultimately provides the composition with from about 0.15 mg to about 5 mg of iodine, per serving or dose. The source of iodine may be any known or otherwise suitable source that is safe and effective for oral administration and is compatible with the essential and other ingredients in the selected product form.

The iodine source preferably provides from about 0.2 mg to about 3.0 mg, including from about 0.25 mg to about 2.0 mg, also including from about 0.3 mg to about 1.1 mg, also including from about 0.4 mg to about 0.9 mg, and also including from about 0.5 mg to about 0.75 mg, of iodine per serving or dose.

Such iodine sources may be provided as separate sources of iodine or as part of other added ingredients such as multivitamin or mineral premixes, many different commercially available sources of which are well known in the various arts. Non-limiting examples of other specific iodine sources include potassium iodide, sodium iodide, iodinated proteins such as iodinated casein, iodinated lipids or other iodinated materials, calcium iodate, molecular or diatomic iodine ($I_2$), and combinations thereof. Inorganic forms of iodine such as potassium iodide are less preferred than protein-bound (i.e. iodinated casein) or diatomic forms ($I_2$). These latter forms are believed to be less thyrotropic than other forms, and thus allow for the formulation and use of higher and more therapeutic iodine doses with reduced toxicity Preferred are those compositions in which at least about 50%, including from about 75% to 100%, by weight of the iodine is selected from the group consisting of potassium iodide, sodium iodide, iodinated proteins, iodinated lipids, calcium iodate, molecular iodine, and combinations thereof.

Iodine is well known for use in treating individuals with fibrocystic breast disease, the clinical benefits of which include a reduction of breast pain and tenderness as well as some resolution of breast tissue nodularity. The extent of such benefits, however, varies depending upon factors such as the specific form and dose of iodine used in the formulation. Due to the potential toxicity associated with excessive iodine consumption, it is essential that the iodine be formulated into the nutritional compositions of the present invention in the serving ranges described herein. It is now believed that this balance between therapeutic benefits and iodine toxicity is best achieved when the formulation includes selenium as an optional active ingredient, which combines with the GLA and iodine components in the formulation to provide a highly effective nutritional product for use in fibrocystic breast disease and other breast-related disease or condition with improved safety from dose-related or inadvertent dosing toxicities associated with iodine supplements.

Macronutrients

The nutritional embodiments of the present invention comprise one or more macronutrients in addition to the essential ingredients described hereinbefore. The macronutrients include proteins, lipids in addition to the GLA component described herein, carbohydrates, and combinations thereof. The nutritional compositions preferably contain all three macronutrients.

The macronutrients in combination with the other essential or added ingredients provide the nutritional composition with at least about 50 kcal, preferably from about 50 kcal to about 1000 kcal of energy per serving or dose. These macronutrients and other ingredients preferably provide the nutritional composition with from about 50 kcal to about 900 kcal, more preferably from about 75 kcal to about 700 kcal, including from about 100 kcal to about 500 kcal, also including from about 150 kcal to about 400 kcal, and also including from about 200 kcal to about 300 kcal, per serving or dose.

Many different sources and types of proteins, lipids, and carbohydrates are known and can be used in the various nutritional embodiments described herein, provided that the selected nutrients are safe and effective for oral administration and are compatible with the essential and other added ingredients.

Carbohydrates suitable for use in the nutritional embodiments may be simple, complex, or variations or combinations thereof. Non-limiting examples of suitable carbohydrates include hydrolyzed or modified starch or cornstarch, maltodextrin, glucose polymers, sucrose, corn syrup, corn syrup solids, rice-derived carbohydrate, glucose, fructose, lactose, high fructose corn syrup, indigestible oligosaccharides (e.g., fructooligosaccharides), honey, sugar alcohols (e.g., maltitol, erythritol, sorbitol), and combinations thereof.

Carbohydrates suitable for use herein also include soluble dietary fiber, non-limiting examples of which include gum arabic, sodium carboxymethyl cellulose, guar gum, citrus pectin, low and high methoxy pectin, oat and barley glucans, carrageenan, psyllium and combinations thereof. Soluble dietary fiber is also suitable as a carbohydrate source herein, non-limiting examples of which include oat hull fiber, pea hull fiber, soy hull fiber, soy cotyledon fiber, sugar beet fiber, cellulose, corn bran, and combinations thereof.

Proteins suitable for use in the nutritional embodiments include hydrolyzed, partially hydrolyzed or non-hydrolyzed proteins or protein sources, and can be derived from any known or otherwise suitable source such as milk (e.g., casein, whey), animal (e.g., meat, fish), cereal (e.g., rice, corn), vegetable (e.g., soy), or combinations thereof. The proteins for use herein can also include, or be entirely or partially replaced by, free amino acids known for use in nutritional products, non-limiting examples of which include tryptophan, glutamine, tyrosine, methionine, cysteine, arginine, and combinations thereof.

Lipids suitable for use in the nutritional embodiments include coconut oil, fractionated coconut oil, soy oil, corn oil, olive oil, safflower oil, high oleic safflower oil, MCT oil (medium chain triglycerides), sunflower oil, high oleic sunflower oil, palm and palm kernel oils, palm olein, canola oil, marine oils, cottonseed oils, and combinations thereof. These lipid nutrients may be used in addition to the GLA component as described hereinbefore.

The concentration or amount of carbohydrate, protein, and carbohydrate in the nutritional embodiments can vary considerably depending upon the particular product form and the various other formulations and targeted dietary needs. These macronutrients are most typically formulated within any of the ranges (embodiments A, B, or C) described in the following table.

The compositions of the present invention may further comprise any of a variety of other vitamins or related nutrients, non-limiting examples of which include vitamin A, vitamin D, vitamin E, vitamin K, thiamine, riboflavin, pyridoxine, vitamin $B_{12}$, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

Liquid Embodiment

The nutritional embodiments of the present invention include liquid product forms comprising the requisite amounts of GLA, iodine, and optional selenium as described herein, as well as the requisite caloric content as also described herein. These liquid nutritional embodiments include emulsions, suspensions, solutions, and even liquid crystalline gels, but are most typically and practically formulated as emulsions or suspensions.

The liquid nutritional embodiments of the present invention are further defined by a volume of at least about 25 ml, preferably from about 50 ml to about 500 ml, including from about 75 ml to about 250 ml, and also including from about 80 ml to about 250 ml, and also including from about 80 ml to about 150 ml, per serving or dose, wherein each serving or dose provides the requisite caloric content as described herein, i.e., at least about 50 kcal, including from about 50 kcal to about 1000 kcal, per serving or dose.

The liquid nutritional embodiments of the present invention include those formulations as described in the following table.

| | Liquid Embodiments | | |
|---|---|---|---|
| Nutrients | Embodiments* | | |
| per each 100 ml | A | B | C |
| Carbohydrate - % total calories | 10-70 | 20-60 | 40-50 |
| Lipid - % total calories | 20-65 | 30-60 | 35-55 |
| Protein - % total calories | 5-40 | 10-30 | 15-25 |
| Selenium (µg/100 ml) | 0-400 | 50-250 | 75-250 |

| | Macronutrients | | | | | |
|---|---|---|---|---|---|---|
| Nutrients | Nutritional Solid | | | Nutritional Liquid | | |
| per serving* | A | B | C | A | B | C |
| Carbohydrate % total calories | 0-100 | 10-70 | 40-50 | 0-100 | 10-70 | 40-50 |
| Lipid % total calories | 0-100 | 20-65 | 35-55 | 0-100 | 20-65 | 35-55 |
| Protein % total calories | 0-100 | 5-40 | 15-25 | 0-100 | 5-40 | 15-25 |
| Serving size solids (g) | 10-250 | 10-100 | 10-60 | — | — | — |
| Serving size liquid (ml) | — | — | — | 50-500 | 75-250 | 80-150 |

*Each numerical value is preceded by the term "about"

-continued

Liquid Embodiments

| Nutrients per each 100 ml | Embodiments* | | |
|---|---|---|---|
| | A | B | C |
| GLA (mg/100 ml) | 100-6000 | 250-3000 | 750-2000 |
| Iodine (mg/100 ml) | 0.15-5 | 0.3-1.1 | 0.4-0.9 |
| Total calories (kcal/100 ml) | 50-500 | 70-250 | 90-150 |

*Each numerical value is preceded by the term "about"

Optional Ingredients

The compositions of the present invention may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, anti-oxidants, emulsifying agents, buffers, additional pharmaceutical actives, additional nutrients as described herein, sweeteners including artificial sweeteners (e.g., saccharine, aspartame, acesulfame K, sucralose) colorants, flavors, thickening agents and stabilizers, emulsifying agents, lubricants, and so forth.

Still other optional ingredients for use in the compositions of the present invention include fish oils or flax seed oil or other n-3 fatty acid-containing oils, wherein such optional oils are used in addition to the GLA-containing oils or materials described herein.

Methods of Use

The methods of the present invention are directed to the administration of the compositions of the present invention to improve breast health in women, wherein a serving or dose of the composition is preferably administered daily as a single, undivided dose, although the serving may also be divided into two or more partial or divided servings or doses to be taken at two or more times during the day. The methods of the present invention include continuous daily administration as well as periodic or limited administration, e.g., one dose every other day, two doses every third day, and so forth, although daily administration is preferred. The compositions may be used over prolonged (e.g., greater than about 12 months) or shorter periods (e.g. from 3-12 months), but are preferably administered on a continuous, daily basis over prolonged periods.

The methods of the present invention include those embodiments directed to the administration of the compositions of the present invention to treat fibrocystic breast disease or other breast related disease or condition, including the reduction of breast pain and tenderness associated with the disease. These methods include the oral administration of the compositions to individuals afflicted with fibrocystic breast disease or other breast-related disease or condition in accordance with the above-described oral administration method.

The methods of the present invention also include those embodiments directed to the use of the compositions of the present invention to reduce mammographic breast density, including a reduction of mammographic breast density in individuals afflicted with fibrocystic breast disease or other breast-related disease or condition. These methods include the oral administration of the compositions to such individuals in accordance with the above-described oral administration method.

The methods of the present invention also include those embodiments directed to the use of the compositions of the present invention to reduce the need for frequent or repeat mammograms in women afflicted with fibrocystic breast disease or other breast-related disease or condition that is otherwise associated with a relatively high mammographic breast density. These methods include the oral administration of the compositions to such individuals in accordance with the above-described oral administration method. Such methods may also result in a reduction in the need for subsequent breast tissue biopsies, which might otherwise have been needed if an elevated mammographic breast density had obscured an accurate reading of the mammogram.

The methods of the present invention also include those embodiments directed to the use of the compositions of the present invention to treat or reduce the risk of developing breast cancer in individuals afflicted with fibrocystic breast disease or other breast-related disease or condition. These methods include the oral administration of the compositions of the present invention to such afflicted individuals in accordance with the above-described oral administration method.

The methods of the present invention also include those embodiments directed to the use of the compositions of the present invention to reduce the progression and spread of breast cancer in women afflicted with breast cancer. These embodiments include the oral administration of the compositions of the present invention to such afflicted individuals in accordance with the above-described oral administration method.

The methods of the present invention also include those embodiments directed to the use of the compositions of the present invention to reduce the risk of recurrence of breast cancer in those women once afflicted with breast cancer. These embodiments include the oral administration of the compositions of the present invention to such women in accordance with the above-described oral administration method.

The methods of the present invention also include those embodiments directed to the use of the compositions of the present invention to treat or reduce breast pain and tenderness associated with fibrocystic breast disease or other breast-related disease or condition, wherein the disease or condition is characterized by moderate to severe cyclic on non-cyclic breast pain and tenderness, continuous or random, and lasting for more than about 4 days, most typically from about 5 to about 14 days, per month, although it is understood that many women suffer from such symptoms on a continuous daily basis.

The methods of the present invention include those embodiments directed to the use of the compositions of the present invention to treat or reduce breast nodules in individuals afflicted with or prone to the development of fibrocystic breast disease. These embodiments include the administration of the compositions of the present invention to individuals afflicted with or prone to the development of fibrocystic breast disease in accordance with the above-described oral administration method.

The methods of the present invention also include those embodiments directed to the use of the compositions of the present invention in women afflicted with fibrocystic breast disease or other breast-related disease or condition, or to women who otherwise manifest a historically high mammographic breast density, to improve their ability to more accurately perform self-breast exams. It is believed that by reducing mammographic breast density via the daily administration of the compositions of the present invention that women can then perform more accurate self-breast exams, which includes the ability to do such exams in women who previously were unable to even perform due to excessive pain and tenderness during any attempt to do a self-breast exam. It is also believed that reduced breast density also results in reduced need for more frequent or repeat mammograms, and may reduce the subsequent risk of developing breast cancer.

The methods of the present invention also include those embodiments directed to the use of the compositions of the present invention to reduce the need for hormones (e.g., danazol, bromocriptine, tamoxifen, raloxifene) or analgesics (e.g., non-steroidal anti-inflammatory agents, opiates) or anti-inflammatory steroids (e.g., predisone, hydrocortisone, prednisolone, methylprednisolone, etc.) for treatment of breast pain and tenderness, including that associated with fibrocystic breast disease or other breast-related disease or condition. These embodiments include the administration of the compositions to individuals afflicted with fibrocystic breast disease or other breast-related disease or condition, or who otherwise manifest with unexplained breast pain and tenderness, in accordance with the above-described oral administration method.

The methods of the present invention also include those methods directed to the use of the compositions of the present invention to provide any one or more of the benefits listed below, wherein the method includes the administration of the compositions of the present invention to individuals afflicted with or otherwise prone to develop fibrocystic breast disease or other breast-related disease or condition in accordance with the above-described oral administration method. The benefits to which each of these embodiments of the methods of the present invention are directed include:

- reduction of pain/tenderness as it interferes with a women's ability to 1) sleep, 2) exercise, 3) lift or carry heavy objects close to chest, 4) ability to have physical contact with others, 5) ability to work/perform effectively at work and/or 6) engage in sexual activity,
- reduction in need for lifestyle adjustments in order to accommodate the pain.
- reduction in use of dietary supplements and/or alternative therapy use for the management of pain,
- works naturally with a women's body to reduce or eliminate breast pain and tenderness,
- weight reduction for some women with daily product administration, and
- perception of improved skin condition in some women upon daily product administration.

The methods of the present invention as described herein are intended to include the use of such methods in individuals unaffected by or not otherwise afflicted with fibrocystic breast diseases or other breast-related disease or condition, for the purpose of preventing, minimizing, or delaying the development of such diseases or conditions over time. For such prevention purposes, the methods of the present invention preferably include continuous, daily administration of the compositions as described herein.

The methods of the present invention are particularly useful in avoiding hormone-based therapies such as danazol, bromocriptine, tamoxifen, and others, especially in women who previously have taken such therapies and are now attempting to maintain or improve their current breast health to thus avoid returning to or reducing the need for such therapies. This is particularly applicable in women who have discontinued such therapies during pregnancy, and after completion of the pregnancy would like to maintain or enhance breath health without the use of such therapies. In these women, the methods of the present invention are particularly useful, especially those directed to the daily administration of a composition as described herein.

Manufacture

The nutritional embodiments of the present invention may be prepared by any known or otherwise effective manufacturing technique for preparing the selected product form. Many such techniques are known for any given product form such as nutritional liquids or nutritional bars and can easily be applied by one of ordinary skill in the art to the nutritional products described herein.

The pharmaceutical embodiments of the present invention can likewise be prepared by any known or otherwise effective manufacturing technique for preparing the selected pharmaceutical product form. Many such techniques are known for any given pharmaceutical product form such as capsules, tablets, liquids, and so forth, and can easily be applied by one of ordinary skill in the art to the pharmaceutical products described herein.

Liquid, milk or soy-based nutritional liquids, for example, may be prepared by first forming an oil and fiber blend containing all formulation oils, any emulsifier, fiber and fat-soluble vitamins. Additional slurries (typically a carbohydrate and two protein slurries) are prepared separately by mixing the carbohydrate and minerals together and the protein in water. The slurries are then mixed together with the oil blend. The resulting mixture is homogenized, heat processed, standardized with any water-soluble vitamins, flavored and the liquid terminally sterilized or aseptically filled or dried to produce a powder.

Other product forms such nutritional bars may be manufactured, for example, using cold extrusion technology as is known and commonly described in the bar manufacturing art. To prepare such compositions, typically all of the powdered components are dry blended together, which typically includes any proteins, vitamin premixes, certain carbohydrates, and so forth. The fat-soluble components are then blended together and mixed with any powdered premixes. Finally any liquid components are then mixed into the composition, forming a plastic like composition or dough. The resulting plastic mass can then be shaped, without further physical or chemical changes occurring, by cold forming or extrusion, wherein the plastic mass is forced at relatively low pressure through a die, which confers the desired shape. The resultant exudate is then cut off at an appropriate position to give products of the desired weight. If desired the solid product is then coated, to enhance palatability, and packaged for distribution.

Solid nutritional embodiments of the present invention may also be manufactured through a baked application or heated extrusion to produce solid product forms such as cereals, cookies, crackers, and similar other product forms. One knowledgeable in the nutrition manufacturing arts is able to select one of the many known or otherwise available manufacturing processes to produce the desired final product.

The compositions of the present invention may, of course, be manufactured by other known or otherwise suitable techniques not specifically described herein without departing from the spirit and scope of the present invention. The present embodiments are, therefore, to be considered in all respects as illustrative and not restrictive and that all changes and equivalents also come within the description of the present invention. The following non-limiting examples will further illustrate the compositions and methods of the present invention.

EXAMPLES

The following examples illustrate specific embodiments of the compositions and methods of the present invention, including some suitable techniques to prepare the compositions. Each exemplified composition may also be formulated by conventional methods as a pharmaceutical composition containing the requisite amounts of GLA, iodine, and optional selenium, and used in accordance with the methods of the present invention. The examples are given solely for the purpose of illustration and are not to be construed as limitations of the present invention, as many variations thereof are possible without departing from the spirit and scope of the invention.

Examples 1-20 illustrate nutritional liquid embodiments of the present invention. Also included are corresponding methods of using the compositions in accordance with the methods of the present invention. The ingredients for each exemplified composition are described in the following table. All ingredient amounts are listed as kg per 1000 kg batch of product, unless otherwise specified.

| Ingredient Table: Examples 1-5 | | | | | |
|---|---|---|---|---|---|
| Ingredient | Example 1 | Example 2 | Example 3 | Example 4 | Example 5 |
| Water | Q.S. | Q.S. | Q.S. | Q.S. | Q.S. |
| Sucrose | 65.6 | 65.6 | 65.6 | 65.6 | 65.6 |
| Borage oil[1] | 4.17 | 10.417 | 20.83 | 31.25 | 39.4 |
| Milk protein isolate | 33.4 | 33.4 | 33.4 | 33.4 | 33.4 |
| Acid casein | 9.45 | 9.45 | 9.45 | 9.45 | 9.45 |
| Mg phosphate dibasic | 6.38 | 6.38 | 6.38 | 6.38 | 6.38 |
| Whey protein concentrate | 5.28 | 5.28 | 5.28 | 5.28 | 5.28 |
| Micronized tricalcium phosphate | 4.27 | 4.27 | 4.27 | 4.27 | 4.27 |
| Avicel ™[2] | 4.00 | 4.00 | 4.00 | 4.00 | 4.00 |
| Flavor[5] | 5.50 | 5.50 | 5.50 | 5.50 | 5.50 |
| Sodium chloride | 2.11 | 2.11 | 2.11 | 2.11 | 2.11 |
| Soy lecithin | 1.64 | 1.64 | 1.64 | 1.64 | 1.64 |
| Potassium citrate | 1.63 | 1.63 | 1.63 | 1.63 | 1.63 |
| Sodium citrate | 1.04 | 1.04 | 1.04 | 1.04 | 1.04 |
| NaOH 20% solution | 0.980 | 0.980 | 0.980 | 0.980 | 0.980 |
| Carrageenan | 0.400 | 0.400 | 0.400 | 0.400 | 0.400 |
| Liquid sucralose | 0.175 | 0.175 | 0.175 | 0.175 | 0.175 |
| Ascorbyl palmitate | 0.0492 | 0.0492 | 0.0492 | 0.0492 | 0.0492 |
| Acesulfame K | 0.0350 | 0.0350 | 0.0350 | 0.0350 | 0.0350 |
| Pyridoxine HCl | 0.0243 | 0.0243 | 0.0243 | 0.0243 | 0.0243 |
| Potassium iodide[3] | 0.00197 | 0.00395 | 0.00526 | 0.00658 | 0.00838 |
| Mixed tocopherols | 0.00820 | 0.00820 | 0.00820 | 0.00820 | 0.00820 |
| Folic acid | 0.00551 | 0.00551 | 0.00551 | 0.00551 | 0.00551 |
| Sodium selenate[4] | 0.000598 | 0.001197 | 0.001795 | 0.00359 | 0.00146 |
| Vitamin $D_3$ | 0.00112 | 0.00112 | 0.00112 | 0.00112 | 0.00112 |
| Vitamin K | 0.000201 | 0.000201 | 0.000201 | 0.000201 | 0.000201 |
| Cyanocobalamin | 0.0000661 | 0.0000661 | 0.0000661 | 0.0000661 | 0.0000661 |

[1]Borage oil contain 24% GLA - ingredient amounts listed as kg of Borage oil
[2]Co-processed cellulose gum and microcrystalline cellulose
[3]Ingredient amounts listed as kg of potassium iodide
[4]Ingredient amounts listed as kg of sodium selenate ($Na_2SeO_4$)
[5]Flavor ingredient amounts listed may vary depending upon flavor selection

| Ingredient Table: Examples 6-10 | | | | | |
|---|---|---|---|---|---|
| Ingredient | Example 6 | Example 7 | Example 8 | Example 9 | Example 10 |
| Water | Q.S. | Q.S. | Q.S. | Q.S. | Q.S. |
| Sucrose | 65.6 | 65.6 | 65.6 | 65.6 | 65.6 |
| Borage oil | 50 | 83.3 | 125 | 104 | 250 |
| Milk protein isolate | 33.4 | 33.4 | 33.4 | 33.4 | 33.4 |
| Acid casein | 9.45 | 9.45 | 9.45 | 9.45 | 9.45 |
| Mg phosphate dibasic | 6.38 | 6.38 | 6.38 | 6.38 | 6.38 |
| Whey protein concentrate | 5.28 | 5.28 | 5.28 | 5.28 | 5.28 |
| Micronized tricalcium phosphate | 4.27 | 4.27 | 4.27 | 4.27 | 4.27 |
| Avicel ™[1] | 4.00 | 4.00 | 4.00 | 4.00 | 4.00 |
| Flavor[5] | 5.50 | 5.50 | 5.50 | 5.50 | 5.50 |
| Sodium chloride | 2.11 | 2.11 | 2.11 | 2.11 | 2.11 |
| Soy lecithin | 1.64 | 1.64 | 1.64 | 1.64 | 1.64 |
| Potassium citrate | 1.63 | 1.63 | 1.63 | 1.63 | 1.63 |
| Sodium citrate | 1.04 | 1.04 | 1.04 | 1.04 | 1.04 |
| NaOH (as 20% solution) | 0.980 | 0.980 | 0.980 | 0.980 | 0.980 |

Ingredient Table: Examples 6-10

| Ingredient | Example 6 | Example 7 | Example 8 | Example 9 | Example 10 |
|---|---|---|---|---|---|
| Carrageenan | 0.400 | 0.400 | 0.400 | 0.400 | 0.400 |
| Liquid sucralose | 0.175 | 0.175 | 0.175 | 0.175 | 0.175 |
| Ascorbyl palmitate | 0.0492 | 0.0492 | 0.0492 | 0.0492 | 0.0492 |
| Acesulfame K | 0.0350 | 0.0350 | 0.0350 | 0.0350 | 0.0350 |
| Pyridoxine HCl | 0.0243 | 0.0243 | 0.0243 | 0.0243 | 0.0243 |
| Potassium iodide | 0.00987 | 0.0118 | 0.0145 | 0.0263 | 0.0658 |
| Mixed tocopherols | 0.00820 | 0.00820 | 0.00820 | 0.00820 | 0.00820 |
| Folic acid | 0.00551 | 0.00551 | 0.00551 | 0.00551 | 0.00551 |
| Sodium selenate | 0.00598 | 0.00957 | 0 | 0 | 0 |
| Vitamin $D_3$ | 0.00112 | 0.00112 | 0.00112 | 0.00112 | 0.00112 |
| Vitamin K | 0.000201 | 0.000201 | 0.000201 | 0.000201 | 0.000201 |
| Cyanocobalamin | 0.0000661 | 0.0000661 | 0.0000661 | 0.0000661 | 0.0000661 |

[1] Borage oil contain 24% GLA - ingredient amounts listed as kg of Borage oil
2. Co-processed cellulose gum and microcrystalline cellulose
3. Ingredient amounts listed as kg of potassium iodide
4. Ingredient amounts listed as kg of sodium selenate ($Na_2SeO_4$)
[5] Flavor ingredient amounts listed may vary depending upon flavor selection

Ingredient Table: Examples 11-15

| Ingredient | Example 11 | Example 12 | Example 13 | Example 14 | Example 15 |
|---|---|---|---|---|---|
| Water | Q.S. | Q.S. | Q.S. | Q.S. | Q.S. |
| Sucrose | 65.6 | 65.6 | 65.6 | 65.6 | 65.6 |
| Evening primrose oil[1] | 7.45 | 18.6 | 20.83 | 37.2 | 70.4 |
| Milk protein isolate | 33.4 | 33.4 | 33.4 | 33.4 | 33.4 |
| Acid casein | 9.45 | 9.45 | 9.45 | 9.45 | 9.45 |
| Mg phosphate dibasic | 6.38 | 6.38 | 6.38 | 6.38 | 6.38 |
| Whey protein concentrate | 5.28 | 5.28 | 5.28 | 5.28 | 5.28 |
| Micronized tricalcium phosphate | 4.27 | 4.27 | 4.27 | 4.27 | 4.27 |
| Avicel ™[2] | 4.00 | 4.00 | 4.00 | 4.00 | 4.00 |
| Flavor[5] | 5.50 | 5.50 | 5.50 | 5.50 | 5.50 |
| Sodium chloride | 2.11 | 2.11 | 2.11 | 2.11 | 2.11 |
| Soy lecithin | 1.64 | 1.64 | 1.64 | 1.64 | 1.64 |
| Potassium citrate | 1.63 | 1.63 | 1.63 | 1.63 | 1.63 |
| Sodium citrate | 1.04 | 1.04 | 1.04 | 1.04 | 1.04 |
| NaOH 20% solution | 0.980 | 0.980 | 0.980 | 0.980 | 0.980 |
| Carrageenan | 0.400 | 0.400 | 0.400 | 0.400 | 0.400 |
| Liquid sucralose | 0.175 | 0.175 | 0.175 | 0.175 | 0.175 |
| Ascorbyl palmitate | 0.0492 | 0.0492 | 0.0492 | 0.0492 | 0.0492 |
| Acesulfame K | 0.0350 | 0.0350 | 0.0350 | 0.0350 | 0.0350 |
| Pyridoxine HCl | 0.0243 | 0.0243 | 0.0243 | 0.0243 | 0.0243 |
| Iodinated casein[3] | 0.0015 | 0.0030 | 0.0040 | 0.0050 | 0.0065 |
| Mixed tocopherols | 0.00820 | 0.00820 | 0.00820 | 0.00820 | 0.00820 |
| Folic acid | 0.00551 | 0.00551 | 0.00551 | 0.00551 | 0.00551 |
| Sodium selenate[4] | 0.000544 | 0.001077 | 0.001633 | 0.00327 | 0.00133 |
| Vitamin $D_3$ | 0.00112 | 0.00112 | 0.00112 | 0.00112 | 0.00112 |
| Vitamin K | 0.000201 | 0.000201 | 0.000201 | 0.000201 | 0.000201 |
| Cyanocobalamin | 0.0000661 | 0.0000661 | 0.0000661 | 0.0000661 | 0.0000661 |

[1] Evening primrose oil contains 14% GLA - ingredient amounts listed as kg of evening primrose oil
[2] Co-processed cellulose gum and microcrystalline cellulose
[3] Ingredient amounts listed as kg of iodine provided by idodinated casein
[4] Ingredient amounts listed as kg of sodium selenite ($Na_2SeO_3$)
[5] Flavor ingredient amounts listed may vary depending upon flavor selection

Ingredient Table: Examples 16-20

| Ingredient | Example 16 | Example 17 | Example 18 | Example 19 | Example 20 |
|---|---|---|---|---|---|
| Water | Q.S. | Q.S. | Q.S. | Q.S. | Q.S. |
| Sucrose | 65.6 | 65.6 | 65.6 | 65.6 | 65.6 |
| Evening primrose oil[1] | 89.3 | 83.3 | 148.7 | 185.7 | 446 |
| Milk protein isolate | 33.4 | 33.4 | 33.4 | 33.4 | 33.4 |

Ingredient Table: Examples 16-20

| Ingredient | Example 16 | Example 17 | Example 18 | Example 19 | Example 20 |
|---|---|---|---|---|---|
| Acid casein | 9.45 | 9.45 | 9.45 | 9.45 | 9.45 |
| Mg phosphate dibasic | 6.38 | 6.38 | 6.38 | 6.38 | 6.38 |
| Whey protein concentrate | 5.28 | 5.28 | 5.28 | 5.28 | 5.28 |
| Micronized tricalcium phosphate | 4.27 | 4.27 | 4.27 | 4.27 | 4.27 |
| Avicel ™[2] | 4.00 | 4.00 | 4.00 | 4.00 | 4.00 |
| Flavor[5] | 5.50 | 5.50 | 5.50 | 5.50 | 5.50 |
| Sodium chloride | 2.11 | 2.11 | 2.11 | 2.11 | 2.11 |
| Soy lecithin | 1.64 | 1.64 | 1.64 | 1.64 | 1.64 |
| Potassium citrate | 1.63 | 1.63 | 1.63 | 1.63 | 1.63 |
| Sodium citrate | 1.04 | 1.04 | 1.04 | 1.04 | 1.04 |
| NaOH (as 20% solution) | 0.980 | 0.980 | 0.980 | 0.980 | 0.980 |
| Carrageenan | 0.400 | 0.400 | 0.400 | 0.400 | 0.400 |
| Liquid sucralose | 0.175 | 0.175 | 0.175 | 0.175 | 0.175 |
| Ascorbyl palmitate | 0.0492 | 0.0492 | 0.0492 | 0.0492 | 0.0492 |
| Acesulfame K | 0.0350 | 0.0350 | 0.0350 | 0.0350 | 0.0350 |
| Pyridoxine HCl | 0.0243 | 0.0243 | 0.0243 | 0.0243 | 0.0243 |
| $I_2$ source[3] | 0.0015 | 0.0030 | 0.0040 | 0.0050 | 0.0065 |
| Mixed tocopherols | 0.00820 | 0.00820 | 0.00820 | 0.00820 | 0.00820 |
| Folic acid | 0.00551 | 0.00551 | 0.00551 | 0.00551 | 0.00551 |
| Sodium selenite[4] | 0.00544 | 0.00870 | 0 | 0 | 0 |
| Vitamin $D_3$ | 0.00112 | 0.00112 | 0.00112 | 0.00112 | 0.00112 |
| Vitamin K | 0.000201 | 0.000201 | 0.000201 | 0.000201 | 0.000201 |
| Cyanocobalamin | 0.0000661 | 0.0000661 | 0.0000661 | 0.0000661 | 0.0000661 |

[1]Evening primrose oil contains 14% GLA - ingredient amounts listed as kg of evening primrose oil
[2]Co-processed cellulose gum and microcrystalline cellulose
[3]Ingredient amounts listed as kg of iodine provide from the source of diatomic iodine
[4]Ingredient amounts listed as kg of sodium selenite ($Na_2SeO_3$)
[5]Flavor ingredient amounts listed may vary depending upon flavor selection The liquid nutritional embodiments of the present invention, including each of the exemplified formulas described above, may be prepared by forming at least three separate slurries, which are then blended together, heat-treated, standardized and aseptically packaged into 32 oz. plastic bottles.

For example, a carbohydrate-mineral slurry is initially prepared by dissolving potassium citrate and sodium citrate in water heated to 60-65° C. Carrageenan is dry blended with equal amounts of sucrose and added to the slurry with agitation. Avicel™ is slowly added to the slurry with agitation, followed by potassium iodide (or other iodine source), sodium chloride, tricalcium phosphate, and magnesium phosphate. The remaining sucrose is added to the slurry and agitated for at least 10 minutes. The temperature of the slurry is maintained at about 68° C. with agitation for a maximum of 8 hours until it is blended with the other slurries described hereinafter.

An oil slurry is prepared by placing the required amount of borage oil (or other GLA source) into a kettle and gently heating it to 23-32° C. with agitation. Lecithin is then mixed into the heated oil, followed by ascorbyl palmitate, mixed tocopherols, vitamin D and vitamin K, all with agitation. The resulting oil slurry is held under low agitation with the heat turned off for no longer than 2 hours until it is blended with the other slurries as described hereinafter.

A protein-water slurry is prepared by dissolving potassium citrate in water at 65-76° C., at which point the resulting solution is held for about 1 minute before slowly adding acid casein under rapid agitation, and held thereafter for another minute before adding a 20% sodium hydroxide solution to bring the protein-solution pH to within a range of 6.4 to 7.1. Milk protein isolate and whey protein concentrate are then blended into the pH-adjusted slurry using a mixing apparatus. The temperature of the slurry is lowered to about 57-60° C. before adding with agitation a 75% whey protein concentrate. The resulting protein-water slurry is held under agitation at 62-68° C. for not longer than 2.5 hours before being blended with the other slurries as described hereinafter.

The protein-water slurry, the oil slurry, and the carbohydrate-mineral slurry are blended together with agitation. The blended slurry is maintained at 48-60° C. for at least 15 minutes, after which the pH measured and adjusted if necessary with dilute potassium hydroxide to a pH of from 6.55 to 6.8.

After waiting a period of not less than 15 minutes nor greater than two hours the blended slurry is subjected to HTST treatment, and homogenization as described as follows: heat the blended slurry to a temperature in the range of about 68-74° C.; emulsify the blended slurry at 900-1,100 psig; homogenize in a range between 3,900-4,100/400-600 psig; pass the mix through a holding tube to assure the mix receives a heat treatment between 73-85° C. for 16 seconds; reduce the temperature to 1-7° C. Store the blended slurry at 1-7° C., preferably with agitation.

Preferably at this time appropriate analytical testing for quality control is conducted. Based upon the test results an appropriate amount of dilution water (10-38° C.) may be added to the blended slurry with agitation.

A vitamin solution, a flavor and a color solution are prepared separately and then added to the blended slurry. The vitamin solution is prepared by heating water to 43-66° C. with agitation, and thereafter adding folic acid, vitamin $B_{12}$, sodium selenate (if any) and then pyridoxine. The vitamin solution is then added to the blended slurry with agitation.

The flavor solution is prepared by adding the required amount of liquid sucralose and Ace K sweeteners to water with agitation. The required amount of artificial flavor is then added. The flavor solution is then added to the blended slurry with agitation.

If necessary, diluted potassium hydroxide is added to the blended slurry such that the product will have a pH in the range of 6.4 to 7.0 after sterilization. The completed product is then placed in suitable containers and subjected to sterilization. Of course, if desired aseptic processing could be employed.

Each of the exemplified nutritional liquids is provided to women afflicted with fibrocystic breast disease or other breast-related disease or condition, including women suffering from moderate to severe cyclic breast pain lasting for more than about 4 days prior to treatment with the nutritional product. Each woman takes 118 ml (approximately 100 kcal) as a single, undivided dose once a day. Women continue taking the daily formula continuously for at least 2-3 months, and in most cases indefinitely as a daily dietary or other supplement. Each woman therefore consumes the nutritional product in accordance with the methods of the present invention, which results in at least some of the women manifesting the following benefits:

1. Amelioration of symptoms associated with fibrocystic breast disease or other breast-related disease or condition, including a reduction in breast tenderness and pain,
2. Reduction in mammographic breast density,
3. Reduction in the risk of developing, progression, and recurrence of breast cancer,
4. Reduction in the need for repeated mammographic x-rays,
5. Amelioration of breast pain and tenderness otherwise associated with moderate to severe cyclic breast pain lasting for more than about 4 days prior to continued daily administration of the nutritional product,
6. Amelioration of breast nodule size and occurrence,
7. Improved ability, including improved accuracy, to perform self-breast exams,
8. Reduction in the need for added analgesics to control breast pain and tenderness,
9. Amelioration of breast pain and tenderness as it interferes with a women's ability to 1) sleep, 2) exercise, 3) lift or carry heavy objects close to chest, 4) ability to have physical contact with others, 5) ability to work/perform effectively at work and/or 6) sexual activity,
10. Reduction in need for lifestyle adjustments in order to accommodate the pain,
11. Reduction in use of dietary supplements and/or alternative therapy use for the management of pain,
12. Avoidance of hormone-based treatments and their associated side effects,
13. Prevention of fibrocystic breast disease or other breast-related diseases or conditions,
14. Weight reduction for some women with daily product administration, and/or
15. Perception of improved skin condition in some women upon daily product administration.

Each of the exemplified nutritional compositions is also formulated in a corresponding pharmaceutical dosage form containing the same GLA, iodine, and optional selenium content as the corresponding nutritional liquid, in single serving or dose, or as multiple dosage forms, but without the other added macronutrients and other ingredients specifically designed for a nutritional product form. The exemplified pharmaceutical dosage forms include capsules and liquids. Each pharmaceutical composition is used in accordance with the methods of the present invention, including those described in association with nutritional liquid embodiments described in Examples 1-20, wherein one or more of the pharmaceutical dosage forms is administered per serving or per day to provide the requisite benefit.

Experiment I

An in-vitro study is conducted to determine the potential effects, if any, that selenium, GLA, iodine, and combinations thereof, might have as important roles in the regulation of tight junctions for cell-cell attachment in endothelial cells and on mammary epithelial cells. In the event such effects are realized, it is also a purpose of the study to determine the molecular cellular mechanism by which the various actives or combinations of actives delivers the effects.

As background, the tight junctions referenced in the study are the apical most structures in epithelial and endothelial cells. The junctions create a physiological barrier by forming a paracellular fence, which helps to maintain distinct tissue spaces and to separate the apical from the lateral plasma membranes. The tight junctions have charge and size selectivity to any trespassing molecules. The tightness of the cellular structure is dependent upon the cell and tissue types. Damage to the cell-cell adhesion and tight junction in the epithelium or endothelium may result in an increase to the permeability of cell layer to fluids and micro/macro-molecules. This may lead to edema and swelling of tissues followed by mastalgia.

The data from the study show that compositions containing any one of selenium, iodine, or GLA have a beneficial effect on reinforcing the function of tight junctions of endothelial cells and on mammary epithelial cells. The data also shows that certain combinations of these actives are especially effective in this regard, especially when used on test cells in the presence of estrogen. This data suggest that the various combinations of these actives are especially effective and useful in nutritional or other formulations to help treat fibrocystic breast disease or other breast-related disease or condition, including breast pain or mastalgia, and are even more effective when the breast-related disease or other condition is estrogen sensitive.

As described below, the study assesses the effect of selenium, iodine, GLA, and various combinations thereof on tight junction function (trans-endothelial/epithelial resistance and paracellular permeability) as carried out on the following human cells: HECV endothelial cells and MDA-MB-231, a highly invasive mammary tumor epithelial cells.

1. Methodology

TER and PCP Measurement

Transendothelial (or Transepithelial) Resistance (TER) is measured with an EVOM volt-ohmmeter, equipped with a pair of STX-2 chopstick electrodes. Briefly, MDA-MB-231 or HECV cells are seeded into the 0.4 µm pore size insert (upper chamber) and allowed to reach full confluence, after which fresh medium is replaced for further experiments. Inserts with cells treated with selenium, iodine, GLA, or combinations thereof, are tested for a period of 0-24 hours. In selected experiments, 17-β-estradial is also included. Electrodes are placed at the upper and lower chambers and resistance measured with the volt-ohmmeter. Shown are net changes at any given time point (TER=(TERt−TERt0))

Paracellular permeability (PCP) is determined using fluorescently labeled dextran FITC-Dextran 40, (molecular weight 40 kDa) added to the upper chamber. Medium from the lower chamber is collected for intervals up to 4 hours after treatment of cells with selenium, iodine, GLA, or combinations thereof. The relative fluorescence from these collections is read on a multi-channel fluorescence reader. Shown are net changes over time (PCR fluorescent unit=PCTt−PCPt0).

Cell Invasion Assay

The escape of a tumor mass from confinement by the surrounding capsule or basement membrane signals its progression from a benign to an actively malignant growth state.

In the case of epithelial cells, this escape begins with dissolution of the basement membrane that normally underlies the epithelium. The process involves cell adhesion, motility, and the secretion of different classes of proteases. Reconstituted basement membrane matrix has been used for the in vitro assessment of cell invasion.

This Cell Invasion Assay utilizes an invasion chamber consisting of a 24-well tissue culture plate with 12 cell culture inserts and an 8 μm pore size polycarbonate membrane. The upper surface of the insert membrane is coated with a uniform layer of dried basement membrane matrix (BMM) solution. The layer of basement membrane solution forms an effective extracellular matrix protein barrier that prevents non-invasive cells from going through the 8 μm pores. Invasive cells, on the other hand, are able to degrade the matrix proteins that occlude the pores and allow them to pass through. Invaded cells cling to the bottom of the polycarbonate membrane that is tissue culture treated to enhance cell attachment. Labeling and dissociation of the invaded cells from the underside of the membrane are performed in one step. After transfer to a 96-well plate, samples can be measured in a microtiter plate fluorescence reader.

Briefly, the invasion chamber is brought to room temperature in a tissue culture hood. 300-400 μl of warm serum-free media are added to the upper compartment of the cell culture inserts to rehydrate the BMM extract layer for 30-60 minutes at room temperature. A cell suspension of MDA-MB-231 breast tumor cells containing 0.5-1.0×106 cells/ml in serum free media is prepared. The pharmacological agents (GLA, iodine or selenium) are added directly to the cell suspension. The rehydration solution is carefully removed without disturbing the matrix-coated membrane followed by addition of 500 μl of media containing 10% fetal bovine serum to the lower chamber. 300-350 μl of the cell suspension solution with or without agents is added to the upper chamber and incubated for 24-48 hours in a CO2 tissue culture incubator. A 500 μl of the cell staining solution is added to the free wells of the plate.

Inserts from the chambers are removed gently by using a forceps without touching the underside of the inserts. The cell suspension solution is discarded and the inserts placed in the wells containing the cell stain/dissociation solution. The attached cells from the underside are dislodged by gently tapping the insert (use a forceps) against the bottom of the 24-well plate two or three times followed by incubate for 30 minutes in a CO2 tissue culture incubator. After incubation, the insert is removed with a forceps and incubated the 24-well plate with the dislodged cells an additional 30 minutes in a CO2 tissue culture incubator. A 200 μl of the solution containing the dislodged cells is transferred to a 96-well plate in duplicate and measured the fluorescence at excitation 485±10 nm and emission 520±10 nm. The results given in relative fluorescence units (RFU) are converted to cell numbers by running a cell standard curve.

2. Results

A. Effect on TER and PCP in Endothelial and Epithelial Cells

From the functional studies carried out it is seen that all three compounds are able to increase junctional function to some extent in human endothelial cells (HECV). Each substance is tested to ascertain a concentration of maximum effect on tight junction function.

Figure 2:
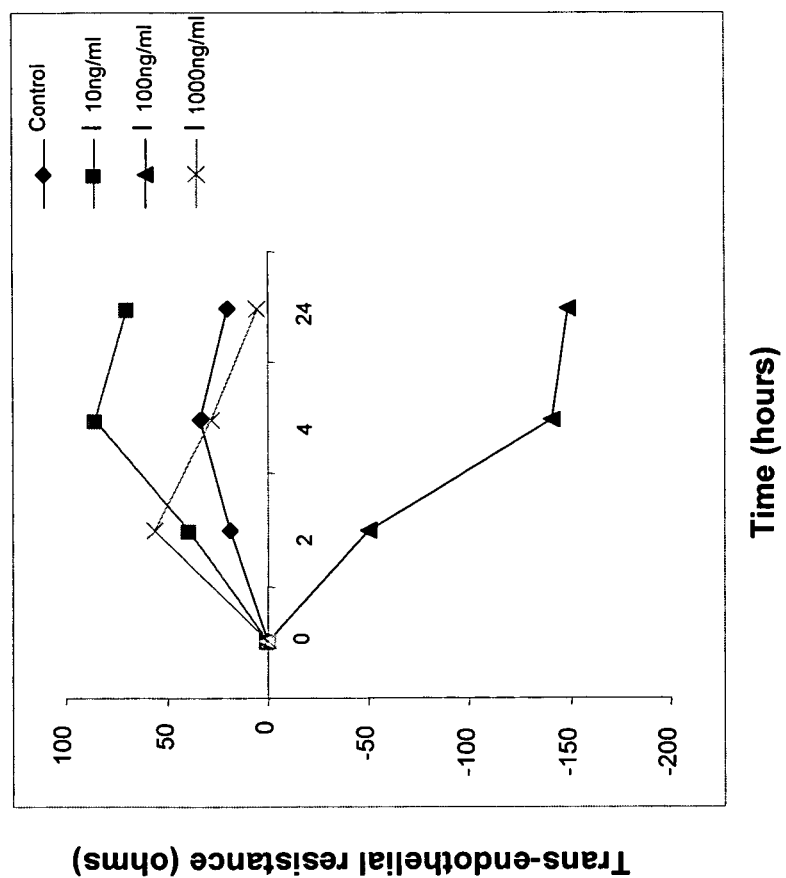
FIG. 2 is a graph of trans-endothilial resistance (ohms) over 24 hours for human endothelial cells (HECV) treated with iodine at 10 ng/ml, 100 ng/ml, and 1000 ng/ml, or untreated (control).
Figure 3:
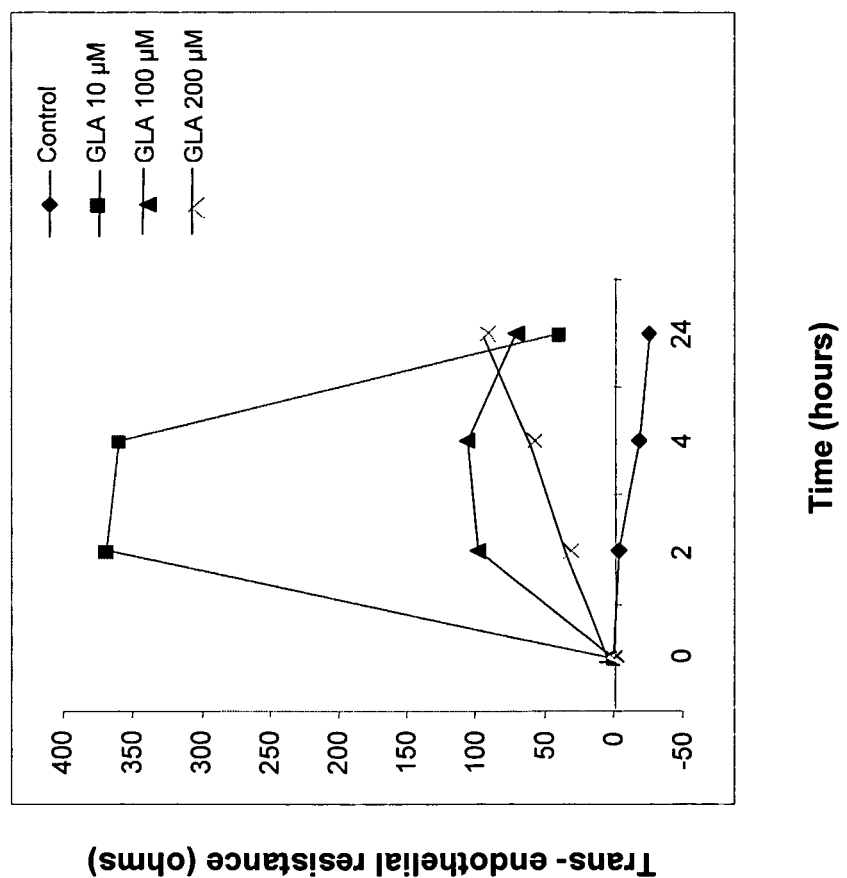
FIG. 3 is a graph of trans-endothilial resistance (ohms) over 24 hours for human endothelial cells (HECV) treated with GLA at 10 μM, 100 μM, and 200 μM, or untreated (control).
Figure 4:
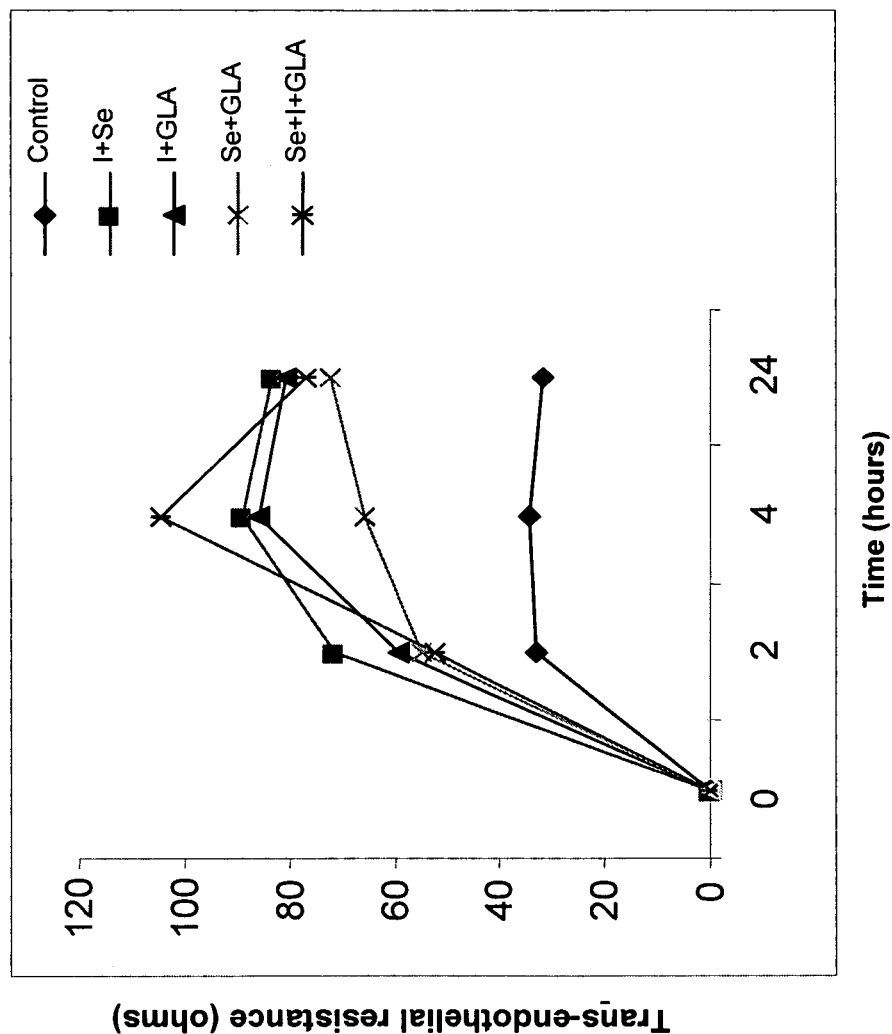
FIG. 4 is a graph of trans-endothilial resistance (ohms) over 24 hours for human endothelial cells (HECV) treated with combinations of selenium (100 ng/ml), iodine (10 ng/ml), and GLA (100 μM) or untreated (control); combinations tested include iodine+selenium, iodine+GLA, selenium+GLA, and selenium+iodine+GLA.

Selenium is shown to have the most effect at 100 ng/ml, iodine at 10 ng/ml, and GLA at 100 μM when evaluating transendothelial resistance (FIG. 1-3). Using these concentrations, combinations of these actives are then used. Again, when using transendothelial resistance (TER), all combinations increase tight junction function over a 4 hour period, with the combination of all three compounds being particularly effective (FIG. 4)

Figure 5:
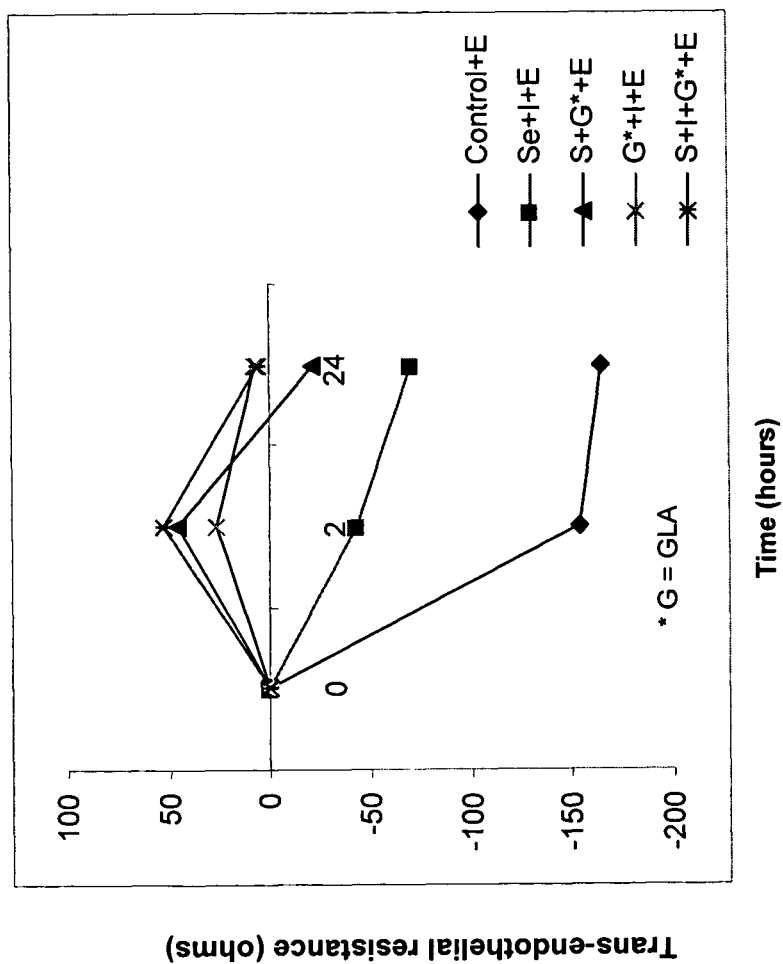
FIG. 5 is a graph of trans-endothilial resistance (ohms) over 24 hours for human endothelial cells (HECV) treated with estrogen (50 μM) and combinations of selenium (100 ng/ml), iodine (10 ng/ml), and GLA (100 μM) or control (estrogen treatment only); combinations include iodine+selenium, iodine+GLA, selenium+GLA, and selenium+iodine+GLA.

It is also found that this effect is noted with endothelial cells treated with estrogen at 50 μM (FIG. 5). Although estrogen is known to reduce tight junction function in endothelial cells, the data from this study indicate that these compounds in combination are able to reverse the effect of estrogen in this cell type.

Figure 6:
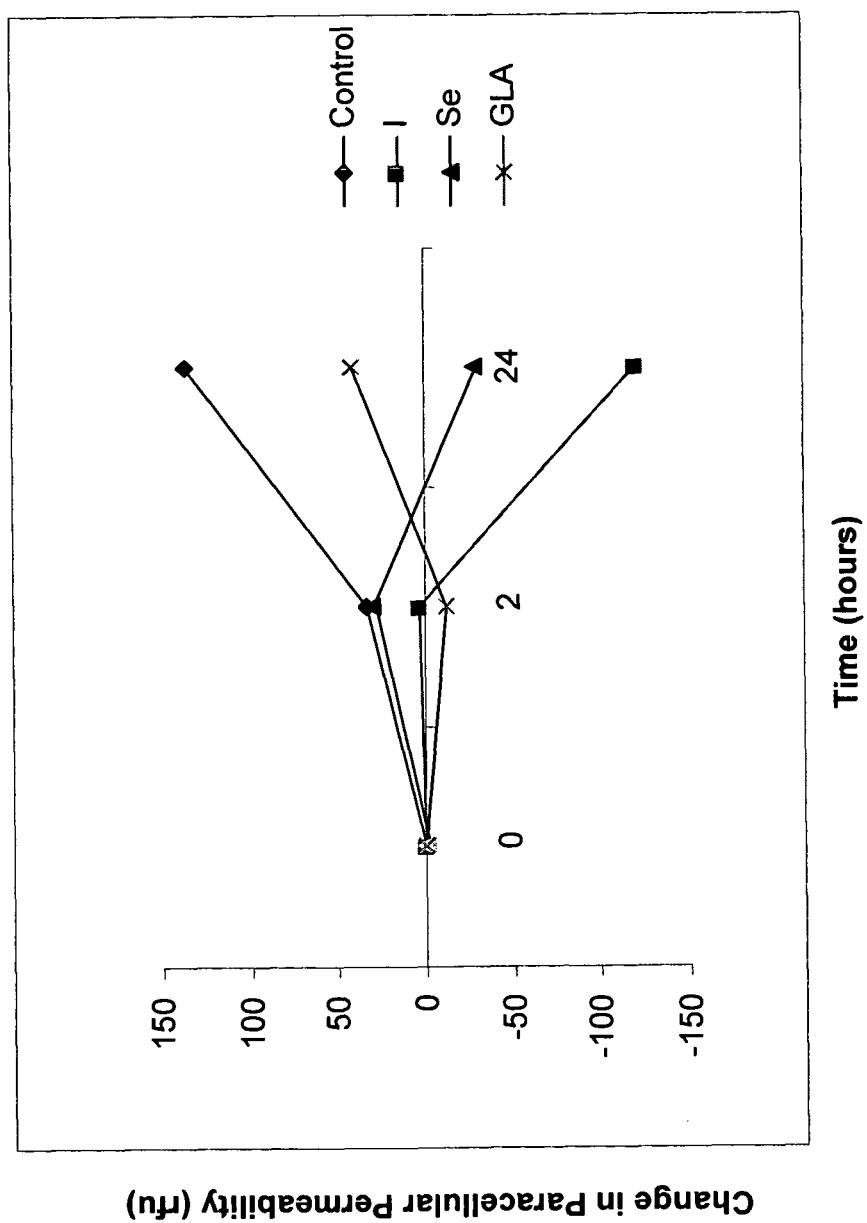
FIG. 6 is a graph of paracellular permeability (rfu) over 24 hours for human endothelial cells (HECV) treated with selenium (100 ng/ml), iodine (10 ng/ml), GLA (100 μM), or untreated (control).
Figure 7:
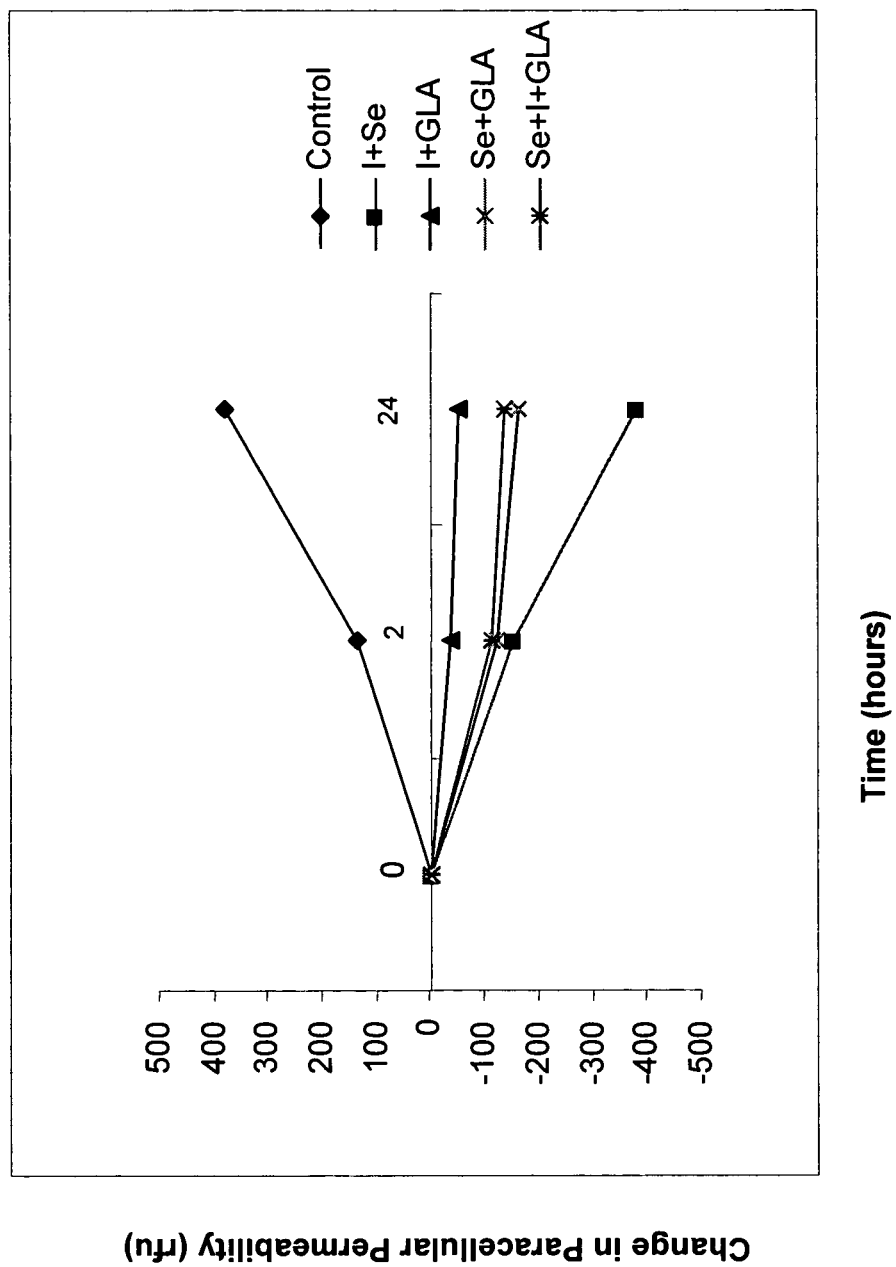
FIG. 7 is a graph of paracellular permeability (rfu) over 24 hours for human endothelial cells (HECV) treated with combinations of selenium (100 ng/ml), iodine (10 ng/ml), and GLA (100 μM), or untreated (control); combinations include iodine+selenium, iodine+GLA, selenium+GLA, and selenium+iodine+GLA.
Figure 8:
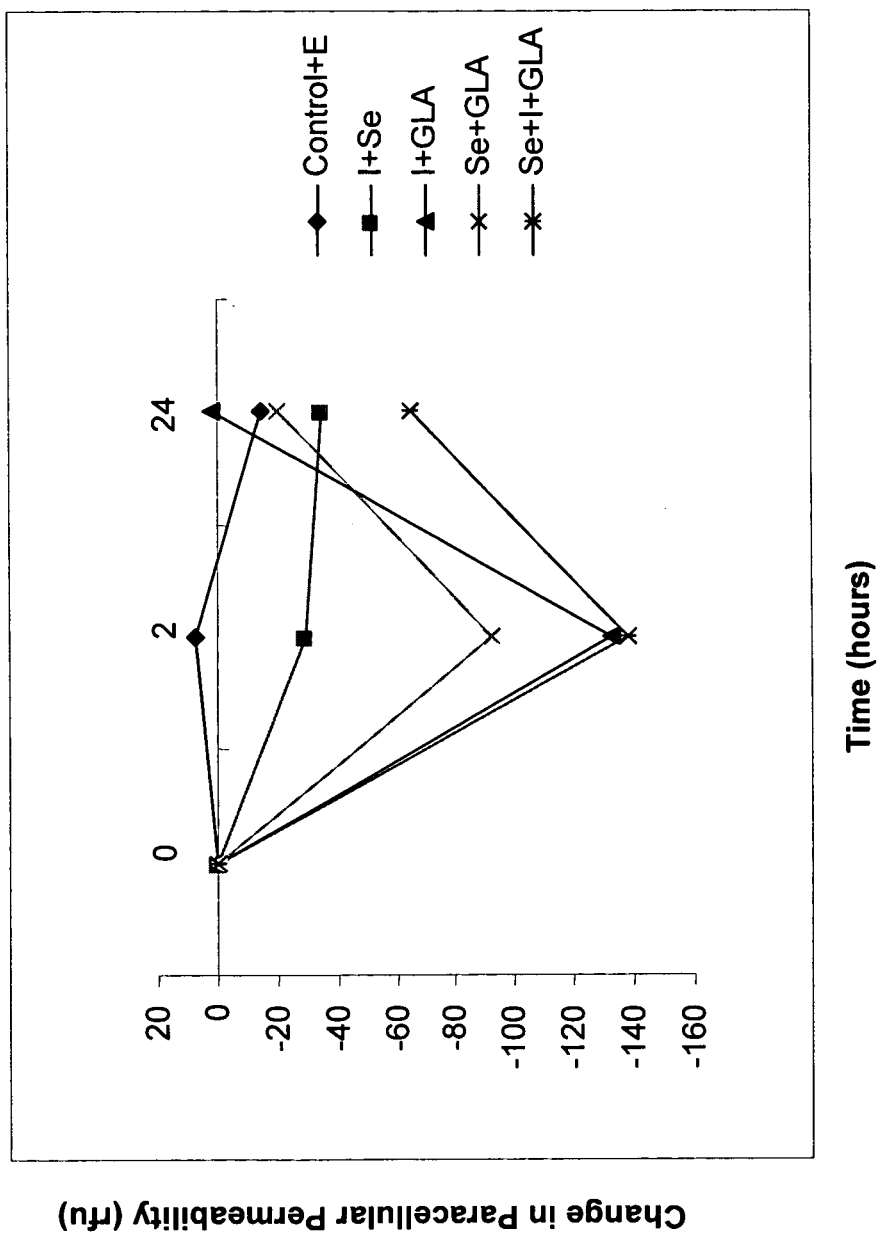
FIG. 8 is a graph of paracellular permeability (rfu) over 24 hours for human endothelial cells (HECV) treated with estrogen (50 μM) and combinations of selenium (100 ng/ml), iodine (10 ng/ml), and GLA (100 μM), or control (estrogen only); combinations with estrogen include iodine+selenium, iodine+GLA, selenium+GLA, and selenium+iodine+GLA.

When evaluating the effect of these compounds using paracellular permeability measurements, there is a significant decrease in permeability in endothelial cells with the compounds individually (FIG. 6). These effects are increased when the compounds are used in combination, with iodine and selenium together being especially interesting in this regard (FIG. 7). The combination of all three actives is effective at negating the detrimental effect of estrogen in endothelial permeability (FIG. 8).

Figure 9:
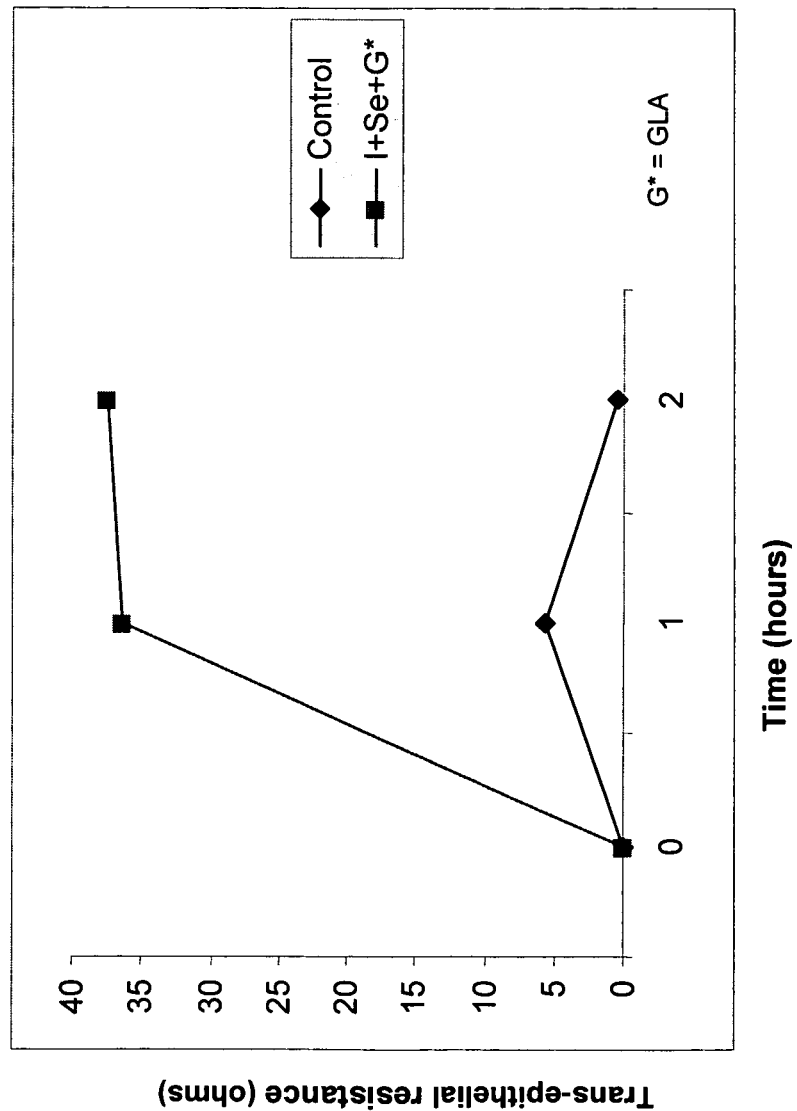
FIG. 9 is a graph of trans-epithelial resistance (ohms) over 24 hours for human breast cancer cells (MDA-MB-231) treated with a combination of selenium (100 ng/ml), iodine (10 ng/ml), and GLA (100 μM), or untreated (control).

These actives, especially when used in combination, may also be effective in treating women with breast cancer. It is observed that all three actives have an effect on the transepithelial resistance of MDA-MB-231 cells, and that a combination of all three actives is especially effective in increasing trans-epithelial resistance in the invasive cell line, MDA-MB-231 (FIG. 9).

B. Effect on Invasion of Breast Cancer Cells

Figure 10:
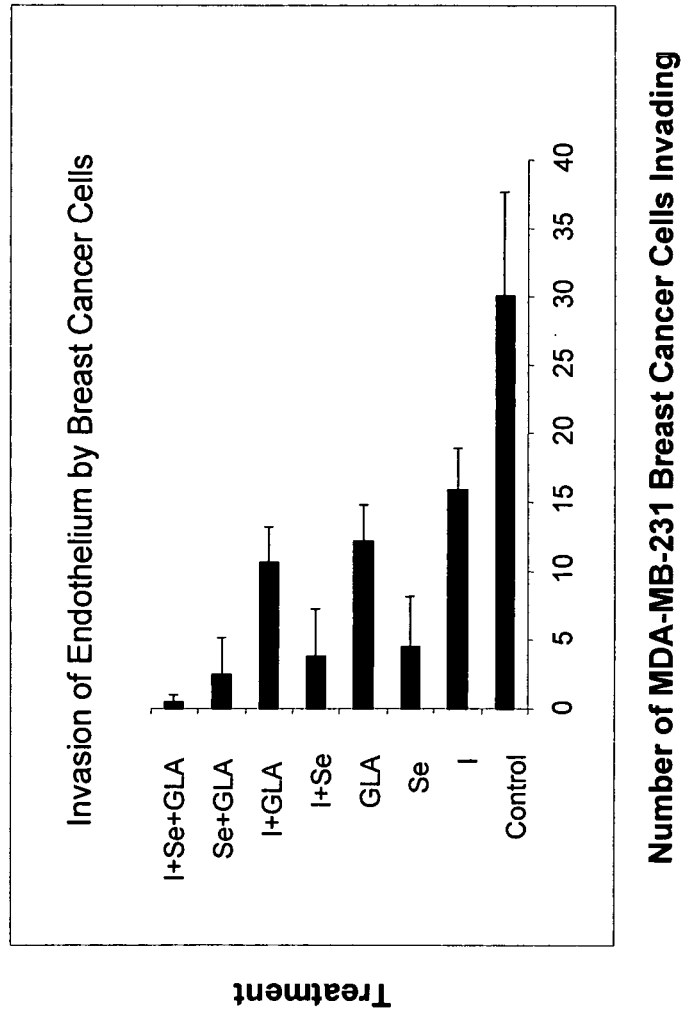
FIG. 10 is a graph showing numbers of breast cancer cells (MDA-MB-231) invading endothelium after treatment with selenium (100 ng/ml), iodine (10 ng/ml), GLA (100 μM), untreated (control), or combinations thereof, including iodine+selenium, iodine+GLA, selenium+GLA, and selenium+iodine+GLA ($p<0.0001$).

The results of cell invasion study are summarized in the graph illustrated in FIG. 10, which shows that various combinations of selenium, iodine, and GLA inhibit invasion by highly aggressive breast cancer cells (MDA-MB-231), thus reducing the potential risk of cancer metastasis, especially in those individuals at risk of recurrence of highly invasive cancer types. The data shows that the combination of selenium, iodine, and GLA is most effective in showing a dramatic result relative to the control.

3. Conclusion

The data from the study establish that all three active ingredients, especially when used in combination, are helpful in modulating the function of tight junctions in both human endothelial and breast cancer cell lines. The data from the study also shows that the active ingredients are especially effective when used in combination, and even more so when used in the presence of estrogen.

This data therefore suggest that the various combinations of selenium, iodine, and GLA are highly effective when used in nutritional or other compositions to treat fibrocystic breast disease or other breast-related disease or condition, especially when the particular conditions are cyclical or estrogen-sensitive afflictions as described herein. In addition, combination of all three ingredients appears to inhibit vascular spread of cancer cells as also described herein.

Experiment II

An in-vitro study is conducted to determine the effects of selenium, GLA, iodine, and combinations thereof on cell proliferation of fibrocystic breast cells, breast cancer cells, and normal breast cells. The purpose of the study is to determine if any of these ingredients would be of benefit in treating individuals afflicted with or at risk of developing breast cell proliferative conditions such as fibrocystic breast disease, breast cancer, or increased breast density, the latter being directly linked to an increased risk of breast cancer.

In this Experiment, we report the effect of GLA, iodine and selenium in the proliferation of different breast epithelial cells, for understanding the cellular events involved in the development of breast cysts and dense tissue and to determine the roles of these compounds in the regulation of cellular pathways.

Materials

Methyl γ linolenate (GLA-ME), sodium selenate, and potassium iodide (KI) are obtained from Sigma-Aldrich, St. Louis, Mo., USA. Initially, GLA-ME is dissolved as a 50 mM stock solution in absolute ethanol while KI and Na-selenate are dissolved as 10 mM stock solutions in Dnase/Rnase free water. ViaLight Plus Cell Proliferation and Cytotoxicity Bio-Assay Kit are purchased from Cambrex Biosciences, East Rutherford, N.J., USA.

Cell Cultures

MCF-7 human breast adenocarcinoma cells (ATCC) are maintained in Eagle's Minimal Essential Medium supplemented with 10% FBS (Gibco-BRL), 1% Penicillin-Streptomycin-Glutamine and 10 nM 17β Estradiol, (Sigma). MCF-10A cells, human fibrocystic mammary gland epithelial cells (ATCC) and HMEC, human mammary gland epithelial cells (Cambrex) are maintained in mammary epithelial complete growth medium (MEGM) containing the Bullet Kit (Cambrex Bio Sciences).

Cell Proliferation Assays

Cells are seeded on 24-well plates at $20\text{-}25 \times 10^3$ cells/well in 0.4-0.5 ml of their respective media. After overnight incubation at 37° C., the cells are then treated with different concentrations of GLA, Se, and KI, either alone or in combinations. Cells with no treatment are the controls. Plates are incubated at 37° C. for 72 hours. Cell proliferation is measured using ViaLight Plus Cell Proliferation and Cytotoxicity BioAssay Kit by quantifying the amount of ATP released from the cells according to manufacture's protocol.

Cell culture plates are warmed up to room temperature for 5 minutes and 200 μl of cell lysis reagent is added to each well. After incubation at room temperature for 10 minutes with intermediate swirling of the plate, 100 μl of the sample from each well is loaded in triplicate in a white 96-well microtiter plate, Dynex Microlite 1+, for vialight assay. The ATP monitoring reagent (AMR) is reconstituted in assay buffer and allowed to equilibrate for 15 minutes at room temperature.

The luminometer and associated WinGlow software program are set up and primed with reconstituted AMR. The plate is placed in the luminometer and 100 μl of reconstituted AMR is dispensed per well. The luminometer is programmed to take one second integrated reading of each appropriate well. The plates are incubated for 2 minutes at room temperature in the luminometer and one second integrated reading of each appropriate well is initiated.

Average RLU (relative luciferase unit) values for each set of triplicate wells, using Winglow software and Microsoft Excel, is calculated and graphed. Effects of various treatments are calculated by plotting the percent of inhibition of cell proliferation versus the concentration of treatment. Percent inhibition of cell proliferation is calculated using the formula:

$$\frac{(\text{Average } RLU \text{ of Control (No treatment)} - \text{Average } RLU \text{ of Treatment})}{\text{Average } RLU \text{ of Control}} \times 100$$

Fatty Acid Analysis

Cells are grown in T75 flasks up to 70-80% confluence before being treated with desired fatty acids conjugated with BSA for 48 hours at 37° C. at various concentrations (0, 50, 100 μM). After incubation, the cells are trypsinized from the flask and the cell suspensions are pooled and collected in 50 ml tubes. Each cell type and each treatment is done in duplicate. Cell suspensions are then centrifuged at 1000 rpm for 10 minutes each. Supernatants are discarded and the pellets suspended in phosphate buffered saline. The cells are washed twice with 10 ml of PBS (Phosphate buffer saline) at each step and centrifuged. The pellets are re-suspended in 10 ml of PBS and counted and the cell numbers are normalized for the experiment. The cell suspension is centrifuged again and the pellets stored at −80° C. until lipid extraction is performed.

Lipids are extracted from the cell pellets according to the laboratory protocol. Briefly, each cell pellet from a 50 ml culture is vortexed with 6 ml of methanol, followed by the addition of 12 ml of chloroform and 100 μg of tridecanoin (as internal standard). The mixture is incubated at 4° C. overnight. The chloroform layer is extracted and filtered through a Whatman filter with one gram of anhydrous sodium sulfate to remove particulates and residual water. Organic solvents are evaporated to dryness at 40° C. under a stream of nitrogen. The extracted lipids are derivatized to fatty acid methyl esters (FAME) for gas chromatography (GC) analysis. Briefly, 2 ml of 0.5 N KOH in methanol is added to the extracted lipid and heated to 95-100° C. for 30 minutes and cooled to room temperature. Approximately 2 ml of 14% boron triflouride in methanol is added, and heating is repeated. After the mixture is cooled, 2 ml of water and 1 ml of hexane are added in order to extract FAME. The gas chromatography mass-spectrometry was carried out. The mass spectrum of a new peak obtained is compared with that of authentic standards and those in database NBS75K.L (National Bureau of Standards).

In Vitro Synthesis of Iodo-Arachidonate

The synthesis of iodo-arachidonate is performed as follows. Briefly, for a 500 ml batch preparation, 2 mmole of KI, 0.75 mmole of arachidonic acid, 0.88 mmole of hydrogen peroxide, and 1205 units of lactoperoxidase are stirred in a phosphate buffer (0.1 M, pH 7.4) for 60 minutes at room temperature. The reaction mixture is then extracted with two volumes of ethyl acetate. After drying on sodium sulfate, the organic phase is evaporated to dryness under reduced pressure. The 6-iodo-5-hydroxy-eicosatrienoic acid-delta-lactone (iodolactone) is converted from arachidonic acid by lactoperoxidase.

After the synthesis reaction has stopped, the unreacted arachidonic acid and other impurities are removed by HPLC. A semi-prep silica column (25 cm×10 mm, 5 μm particle size) and a mobile phase of hexane/2-propanol/ethyl acetate/10% formic acid in 2-propanol (80/10/10/1) at 2 ml/minute are used. Column temperature is maintained at 40° C. The HPLC fraction containing the iodolactone is then collected and concentrated prior to analysis by gas chromatography-mass selective detector (GC-MSD) which is used to characterize the purified iodo-arachidonate or iodolactone.

Results

The Experiment II shows that GLA, iodine and selenium, in addition to improving cell-to-cell attachment in endothelial or breast epithelial cells as demonstrated in Experiment 1, are also able to control proliferation of fibrocystic and breast cancer cells.

Figure 11:
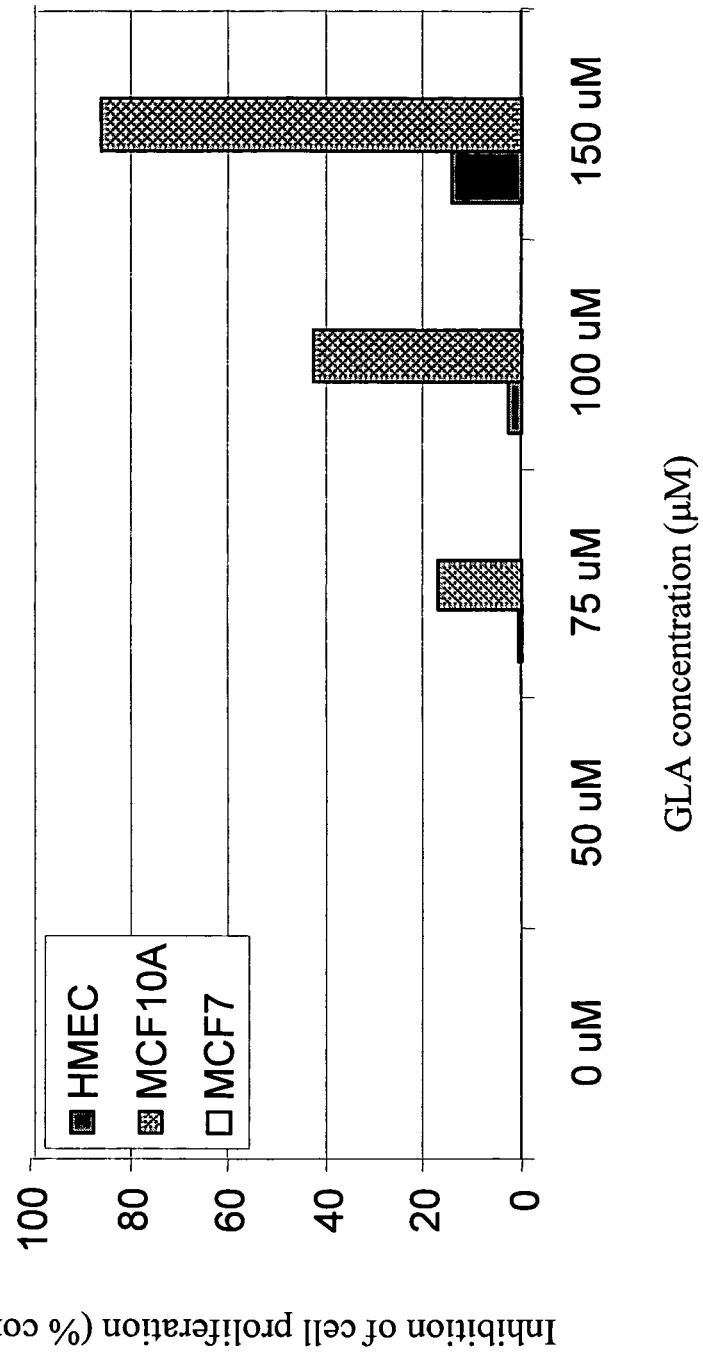
FIG. 11 is a graph showing percent inhibition of cell proliferation of human breast cancer cells (MCF7) and fibrocystic breast cells (MCF10A) relative to that of normal breast cells as a control (HMEC), all after treatment with GLA at 0 μM, 50 μM, 75 μM, 100 μM, and 150 μM.
Figure 12:
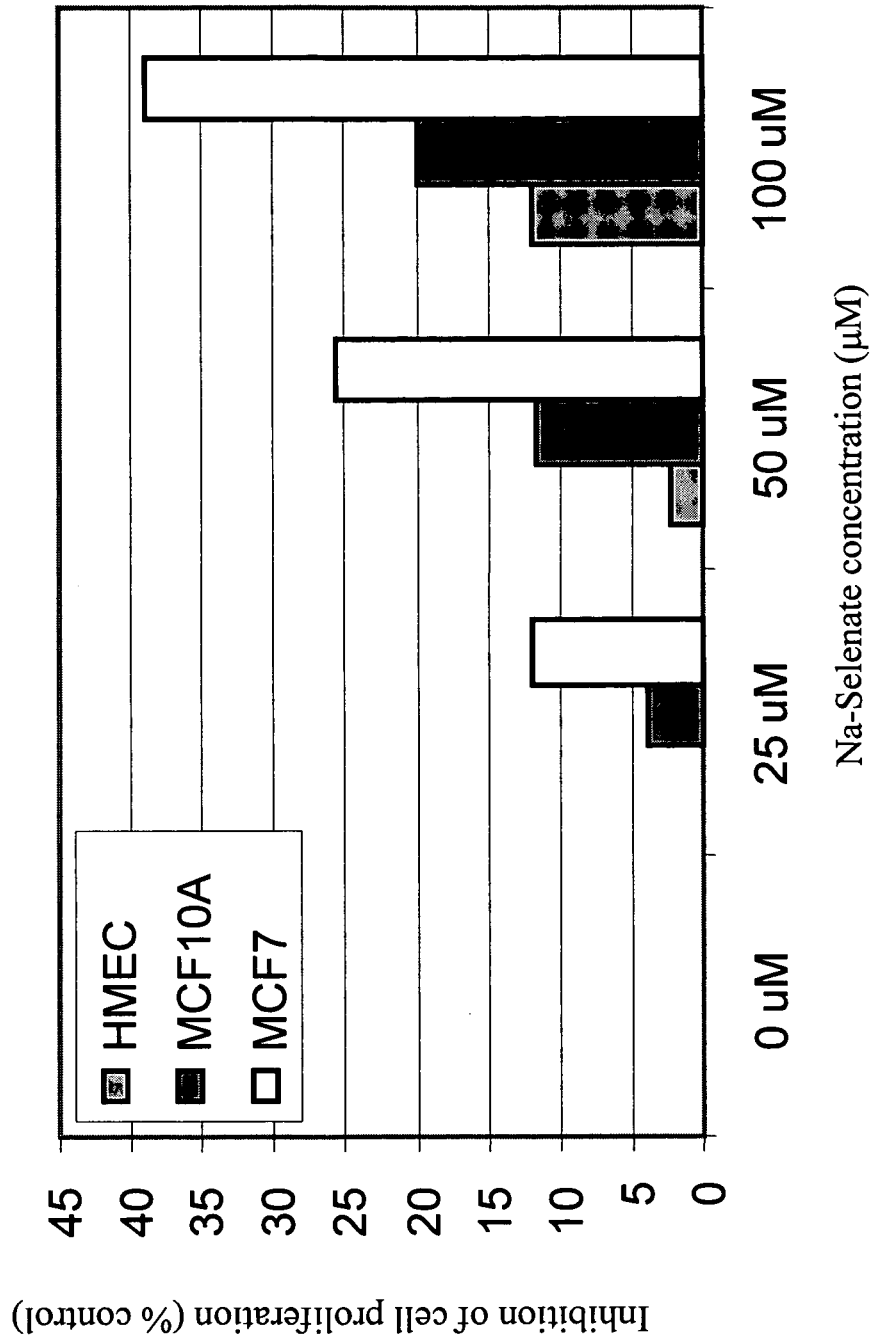
FIG. 12 is a graph showing percent inhibition of cell proliferation of human breast cancer cells (MCF7) and fibrocystic breast cells (MCF10A) relative to that of normal breast cells as a control (HMEC), all after treatment with sodium selenate at 0 μM, 25 μM, 50 μM, and 10 μM.
Figure 13:
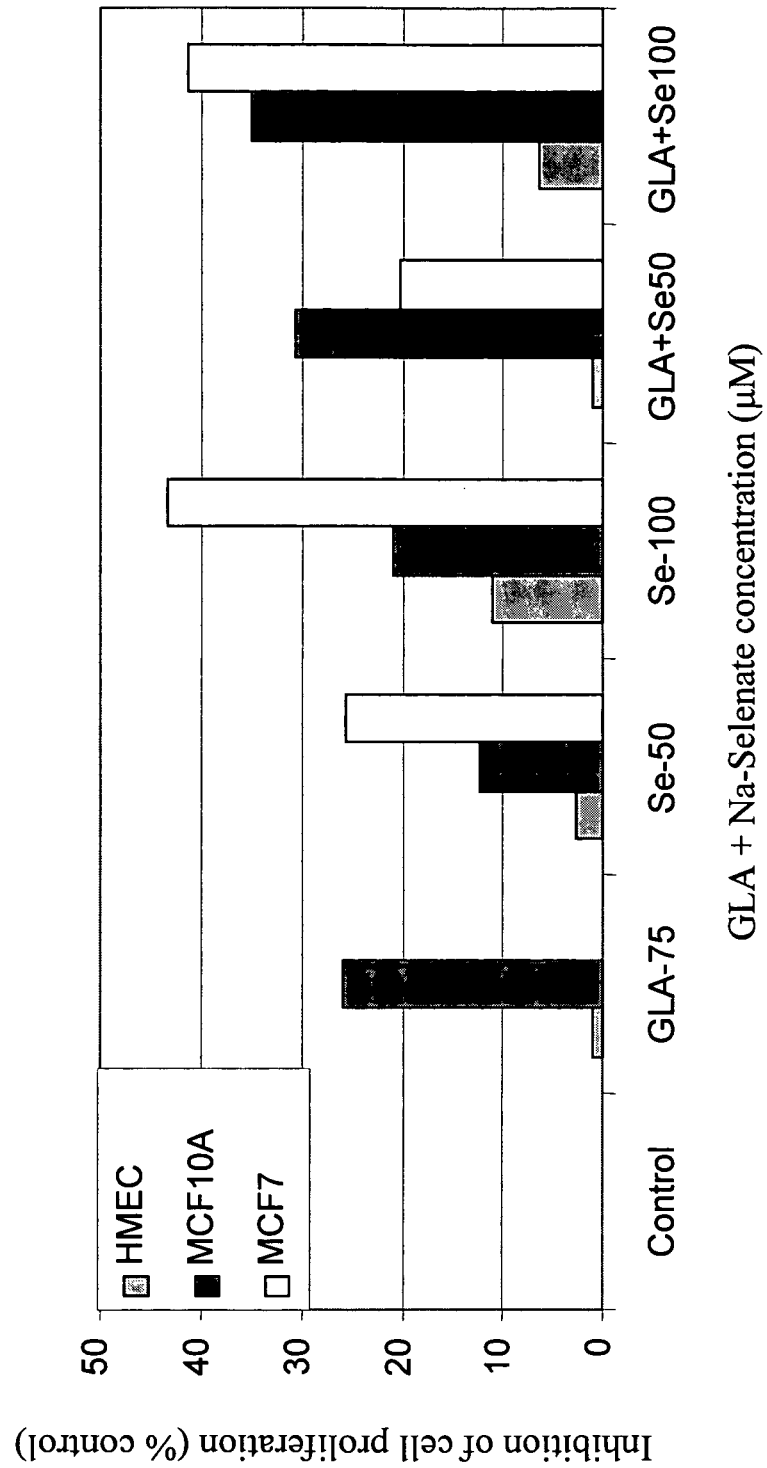
FIG. 13 is a graph showing percent inhibition of cell proliferation of human breast cancer cells (MCF7) and fibrocystic breast cells (MCF10A) relative to that of normal breast cells as a control (HMEC), all after treatment with sodium selenate (50 μM or 100 μM), GLA (75 μM), or combinations of GLA and sodium selenate (GLA 75 μM with either sodium selenate at 50 μM or 100 μM).

The effect of GLA on proliferation of normal (HMEC), fibrocystic (MCF10A and breast cancer (MCF7) cells is tested by treating the cells at increasing concentrations of GLA for 72 hours. The results show that GLA has significant anti-proliferative activity on fibrocystic cells (MCF10A) with no effect on MCF 7 or HMEC cells (FIG. 11). Treatment with selenium has anti-proliferative activity on both MCF7 and MCF10A cells but no relative effect on normal HMEC cells (FIG. 12). Thus, GLA and selenium have a growth inhibitory effect specifically on fibrocystic and breast cancer cells without affecting the growth of normal breast cells. Combinations of GLA and selenium have an enhanced effect on the anti-proliferative activity on MCF10A cell growth (25-35% increase in inhibition by combination of GLA and selenium) (FIG. 13).

Figure 14:
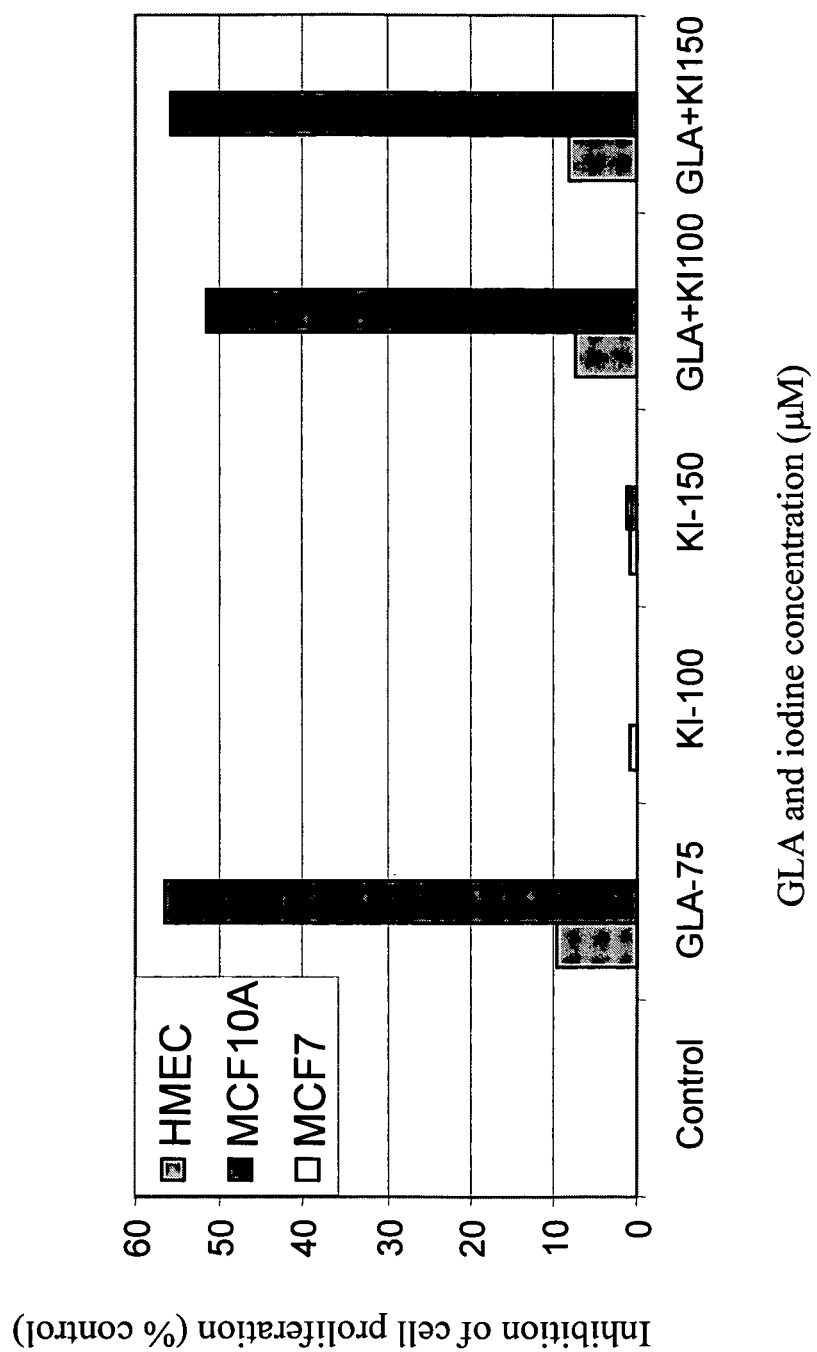
FIG. 14 is a graph showing percent inhibition of cell proliferation of human breast cancer cells (MCF7) and fibrocystic breast cells (MCF10A) relative to that of normal breast cells as a control (HMEC), all after treatment with potassium iodide (100 μM or 150 μM), GLA (75 μM), or combinations of GLA and potassium iodide (GLA 75 μM with potassium iodide at 100 μM or 150 μM).

Iodine, however, when used alone or in combination with GLA, does not show any anti-proliferative effect on fibrocystic or breast cancer cells (FIG. 14), even though it is well known that iodine inhibits proliferation of thyroid follicular cells (e.g., controls goiter development). The anti-proliferative effect of iodine on thyroid cells appears to be mediated by a lipid conjugate of iodine, iodo-arachidonate, an iodolipid formed in thyroid cells by the action of thyroperoxidase on iodine and arachidonic acid.

Figure 15:
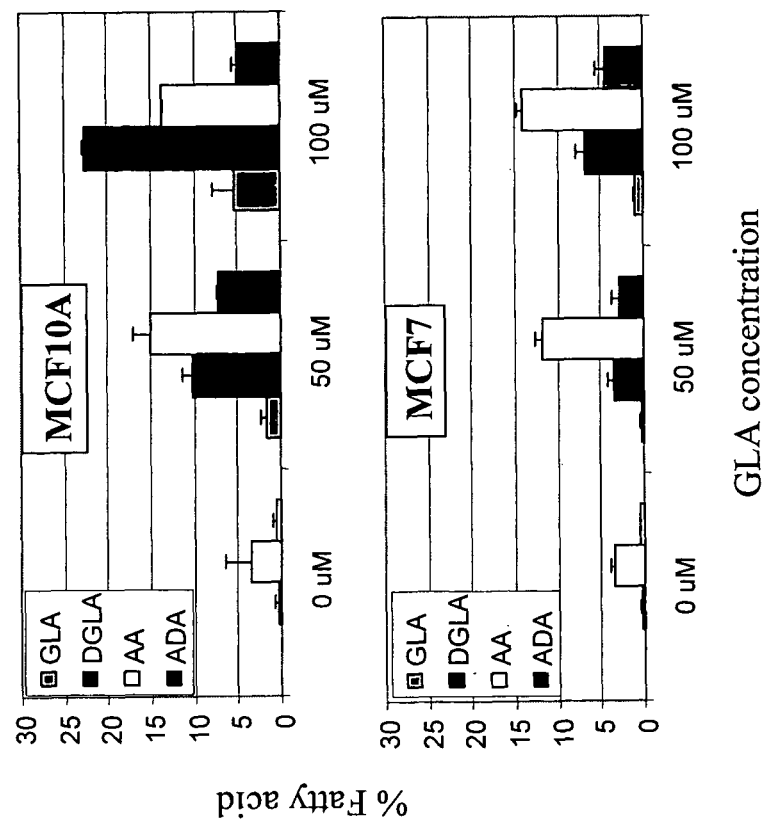
FIG. 15 is a graph showing fatty acid profiles (% fatty acids relative to total fatty acid content in the extracted lipid from the cell) of fibrocystic breast cells (MCF0A) and human breast cancer cells (MCF7) after treatment with GLA at 0 μM, 50 μM, or 100 μM.
Figure 16:
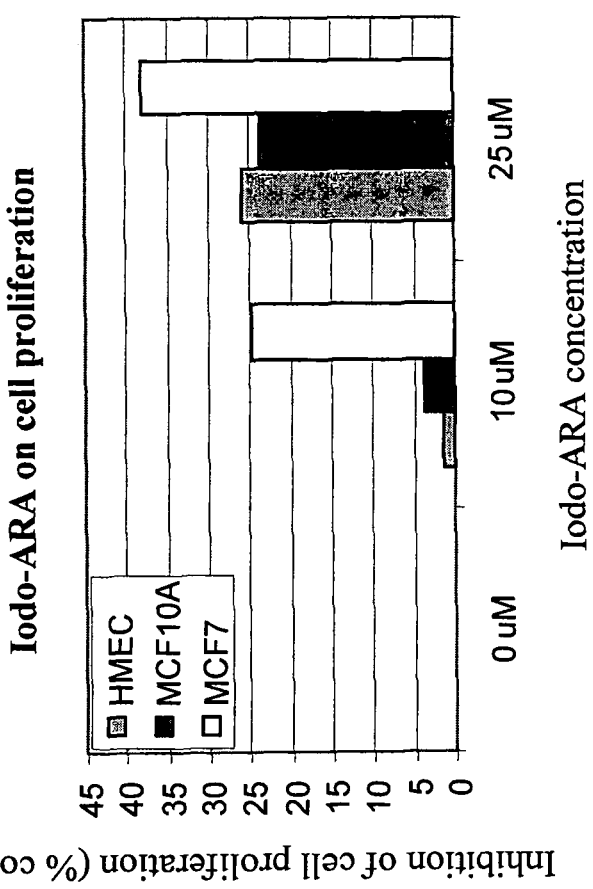
FIG. 16 is a graph showing inhibition of cell proliferation of human breast cancer cells (MCF7), fibrocystic breast cells (MCF10A), and normal breast cells (HMEC) after treatment with Iodo-ARA at 0 μM, 10 μM, and 25 μM.

Interestingly, a similar peroxidase enzyme, lactoperoxidase that is expressed specifically in mammary gland and saliva is also able to synthesize the same iodolipid conjugate in-vitro when arachidonic acid is incubated with KI in the presence of purified lactoperoxidase. It is believed that the arachidonic acid produced in breast tissue can be converted to iodo-arachidonate conjugate by the action of lactoperoxidase enzyme. It has been shown that over-production of arachidonic acid in cells leads to the production of more PGE2 prostaglandin that plays a key role in promoting inflammation as well as cell proliferation or differentiation. Indeed, the treatment of MCF10A or MCF7 with GLA in the present study leads to an increased production of arachidonic acid due to a high delta-5 desaturase activity in both MCF10A and MCF7 cells (FIG. 15). Since iodine is unable to possess anti-proliferative activity on MCF10A or MCF7 cells, it is possible that in-vitro cultured cells (MCF10A or MCF7) are unable to express lactoperoxidase enzyme for the conversion of ARA to iodo-lipid. To address this point, we made iodo-arachidonate in vitro and test its ability on the proliferation of breast epithelial cells. Our data indicate that iodo-arachidonate has significant inhibitory effect on the proliferation of MCF7 cancer cells (FIG. 16).

Thus, the results presented in this application demonstrate the roles of GLA, iodine and selenium in the regulation of different cellular events related to the onset of fibrocystic breast as well as mammographic breast density.

CONCLUSION

Experiments I and II show that GLA, selenium, and iodine may be useful in treating individuals with fibrocystic breast disease or other breast related affliction including benign and malignant breast cancer. The use of these compounds for treating such individuals is based at least in part on in vitro data from the experiments (Experiments I and II) which support the following observations:

1. Defined combinations of GLA, selenium, and/or iodine improve cell-cell attachment in endothelial or breast epithelial cells.
2. Defined combinations of GLA, selenium, and/or iodine can reverse the effect of estrogen in breast endothelial and epithelial cells.
3. Defined combinations of GLA, selenium, and/or iodine can inhibit vascular spread of breast cancer cells.
4. Defined combinations of GLA, selenium, and/or iodine show anti-proliferative activity on fibrocystic and breast cancer cells.
5. Iodine can make iodo-ARA by the action of lactoperoxidase enzyme expressed in breast tissue and iodo-ARA is shown to have anti-proliferative effects on breast cancer cells.

What is claimed is:

1. An oral nutritional composition for improving breast health in women, said composition comprising per serving or dose:

(A) from about 250 mg to about 6000 mg gamma linolenic acid,
(B) from about 0.15 mg to about 5 mg iodine,
(C) from about 25 μg to about 400 μg of selenium, and
(D) fat, protein, carbohydrate, or combinations thereof, wherein the amount of protein is within a range of 2 g to about 20 g,
wherein the oral nutritional composition provides from about 50 kcal to about 1000 kcal of energy per serving or dose.

2. The oral nutritional composition of claim 1 wherein the composition comprises from about 70 μg to about 250 μg of selenium per serving or dose.

3. The oral nutritional composition of claim 1 wherein at least about 50% by weight of the selenium is selected from the group consisting of sodium selenate, sodium selenite, selenium oxide, selenium amino acid complex, L-selenomethionine, selenium-rich yeast, and combinations thereof.

4. The oral nutritional composition of claim 1 wherein the composition provides from about 50 kcal to about 500 kcal of energy per serving or dose.

5. The oral nutritional composition of claim 1 wherein the composition provides from about 100 kcal to about 300 kcal of energy per serving or dose.

6. The oral nutritional composition of claim 1 wherein the composition comprises from about 250 mg to about 2000 mg of gamma linolenic acid per serving or dose.

7. The oral nutritional composition of claim 1 wherein at least about 50% by weight of the gamma linolenic acid is provided by an oil selected from the group consisting of borage oil, black currant seed oil, evening primrose oil, transgenic vegetable oil containing at least about 20% by weight of GLA, and combinations thereof.

8. The oral nutritional composition of claim 1 wherein the composition further comprises borage oil as a source of gamma linolenic acid.

9. The oral nutritional composition of claim 1 wherein the composition comprises from about 0.25 mg to about 1.1 mg of iodine per serving or dose.

10. The oral nutritional composition of claim 1 wherein at least about 50% by weight of the iodine is selected from the group consisting of potassium iodide, sodium iodide, iodinated proteins, calcium iodate, iodinated lipids, molecular iodine, and combinations thereof.

11. The oral nutritional composition of claim 1 wherein the composition is a medical food.

12. The oral nutritional composition of claim 1 wherein from about 10% to about 70% of the total calories provided by the composition are from carbohydrates, from about 20% to about 65% of the total calories provided by the composition are from lipid, and from about 5% to about 40% of the total calories provided by the composition are from protein, wherein the composition provides from about 50 to about 500 kcal of energy per serving or dose.

13. An oral nutritional liquid for improving breast health in women, said liquid comprising per each 100 ml of the liquid:

(A) from about 250 mg to about 6000 mg gamma linolenic acid,
(B) from about 0.15 mg to about 5 mg iodine,
(C) from about 25 μg to about 400 μg of selenium, and
fat, protein, carbohydrate, or combinations thereof, wherein the amount of protein is within a range of 2 g to about 20 g,
wherein the oral nutritional liquid provides from about 50 kcal to about 500 kcal of energy per 100 ml.

14. The oral nutritional liquid of claim 13 wherein the nutritional liquid comprises from about 70 µg to about 250 µg of selenium per each 100 ml of the liquid.

15. The oral nutritional liquid of claim 13 wherein the nutritional liquid provides from about 70 kcal to about 400 kcal of energy per each 100 ml and wherein from about 10% to about 70% of the total calories provided by the nutritional liquid are from carbohydrates, from about 20% to about 65% of the total calories provided by the nutritional liquid are from lipid, and from about 5% to about 40% of the total calories provided by the nutritional liquid are from protein.

16. The oral nutritional liquid of claim 13 wherein the nutritional liquid provides from about 100 kcal to about 300 kcal per each 100 ml of the liquid.

17. The oral nutritional liquid of claim 13 wherein at least about 50% by weight of the selenium is selected from the group consisting of sodium selenate, sodium selenite, selenium oxide, selenium amino acid complex, L-selenomethionine, selenium-rich yeast, and combinations thereof.

18. The oral nutritional liquid of claim 13 wherein the nutritional liquid comprises from about 250 mg to about 2000 mg of gamma linolenic acid per each 100 ml of the liquid.

19. The oral nutritional liquid of claim 13 wherein at least about 50% by weight of the gamma linolenic acid is provided by an oil selected from the group consisting of borage oil, black currant seed oil, evening primrose oil, transgenic vegetable oil containing at least about 20% by weight of gamma linolenic acid, and combinations thereof.

20. The oral nutritional liquid of claim 13 wherein the composition further comprises borage oil as a source of gamma linolenic acid.

21. The oral nutritional liquid of claim 13 wherein the nutritional liquid comprises from about 0.25 mg to about 1.1 mg of iodine per each 100 ml of the liquid.

22. The oral nutritional liquid of claim 13 wherein at least about 50% by weight of the iodine is selected from the group consisting of potassium iodide, sodium iodide, iodinated proteins, iodinated lipids, calcium iodate, molecular iodine, and combinations thereof.

23. The oral nutritional liquid of claim 13 wherein the nutritional liquid is a medical food.

24. A method of treating fibrocystic breast disease or other breast-related disease or condition, said method comprising the daily oral administration of the composition of claim 1 to individuals afflicted with fibrocystic breast disease or other breast-related disease or condition.

25. A method of treating fibrocystic breast disease or other breast-related disease or conditions said method comprising the daily oral administration of the composition of claim 13 to individuals afflicted with fibrocystic breast disease or other breast-related disease or condition.

26. A method of treating breast pain and tenderness in women, said method comprising the daily oral administration of the composition of claim 1 to such individuals.

27. A method of treating breast pain and tenderness in women, said method comprising the daily oral administration of the composition of claim 13 to such individuals.

28. A method of treating mammographic breast density in women, said method comprising the daily oral administration of the composition of claim 1 to such individuals.

29. A method of reducing mammographic breast density in women, said method comprising the daily oral administration of the composition of claim 13 to such individuals.

30. A method of reducing the risk of developing breast cancer in individuals afflicted with fibrocystic breast disease or other breast-related disease or condition, said method comprising the daily oral administration of the composition of claim 1 to such individuals.

31. A method of reducing the risk of developing breast cancer in individuals afflicted with fibrocystic breast disease or other breast-related disease or condition, said method comprising the daily oral administration of the composition of claim 13 to such individuals.

32. A method of treating fibrotic or cancerous cell proliferation in the breasts of women, said method comprising the daily oral administration of the composition of claim 1.

33. A method of treating fibrotic or cancerous cell proliferation in the breasts of women, said method comprising the daily oral administration of the composition of claim 13.

34. A method of treating breast nodule size and formation in individuals afflicted with fibrocystic breast disease or other breast-related disease or condition, said method comprising the daily oral administration of the composition of claim 1 to such individuals.

35. A method of treating breast nodule size and formation in individuals afflicted with fibrocystic breast disease or other breast-related disease or condition, said method comprising the daily oral administration of the composition of claim 13 to such individuals.

36. A method of improving the accuracy of breast self-examinations in individuals afflicted with fibrocystic breast disease or other breast-related disease or condition, said method comprising the daily oral administration of the composition of claim 1 to such individuals.

37. A method of improving the accuracy of breast self-examinations in individuals afflicted with fibrocystic breast disease or other breast-related disease or condition, said method comprising the daily oral administration of the composition of claim 13 to such individuals.

38. A method of treating cyclic breast pain and tenderness in individuals afflicted with fibrocystic breast disease or other breast-related disease or condition, said method comprising the daily oral administration of the composition of claim 1 to such individuals.

39. A method of treating cyclic breast pain and tenderness in individuals afflicted with fibrocystic breast disease or other breast-related disease or condition, said method comprising the daily oral administration of the composition of claim 13 to such individuals.

40. A method of reducing the use of or need for analgesics, anti-inflammatory agents, hormonal agents, or combinations thereof, in individuals afflicted with fibrocystic breast disease or other breast-related disease or condition, said method comprising the daily oral administration of the composition of claim 1 to such individuals.

41. A method of reducing the use of or need for analgesics, anti-inflammatory agents, hormonal agents, or combinations thereof, in individuals afflicted with fibrocystic breast disease or other breast-related disease or condition, said method comprising the daily oral administration of the composition of claim 13 to such individuals.

42. A method of treating premenstrual breast pain and tenderness in women, said method comprising the daily oral administration of the composition of claim 1 to such individuals.

43. A method of treating premenstrual breast pain and tenderness in women, said method comprising the daily oral administration of the composition of claim 13 to such individuals.

44. A method of reducing the need for frequent or repeat mammograms in women afflicted with fibrocystic breast disease or other breast-related disease or condition otherwise associated with a relatively high mammographic breast density, said method comprising the daily oral administration of the composition of claim 1 to such women.

45. A method of reducing the need for frequent or repeat mammograms in women afflicted with fibrocystic breast disease or other breast-related disease or condition otherwise associated with a relatively high mammographic breast density, said method comprising the daily oral administration of the composition of claim 13 to such women.

46. A method of treating fibrocystic breast disease or other breast-related disease or condition, said method comprising the daily oral administration of the composition of claim 1 to individuals afflicted with estrogen-sensitive fibrocystic breast disease or other breast-related disease or condition.

47. A method of treating fibrocystic breast disease or other breast-related disease or condition, said method comprising the daily oral administration of the composition of claim 13 to individuals afflicted with estrogen-sensitive fibrocystic breast disease or other estrogen-sensitive breast-related disease or condition.

48. A method of reducing the progression and spread of breast cancer in women afflicted with breast cancer, said method comprising the daily oral administration of the composition of claim 1.

49. A method of reducing the progression and spread of breast cancer in women afflicted with breast cancer, said method comprising the daily oral administration of the composition of claim 13.

50. A method of reducing the risk of recurrence of breast cancer in women once afflicted with breast cancer, said method comprising the daily oral administration of the composition of claim 1.

51. A method of reducing the risk of recurrence of breast cancer in women once afflicted with breast cancer, said method comprising the daily oral administration of the composition of claim 13.

52. An oral nutritional composition for improving breast health in women, said composition comprising per serving or dose:
- (A) from about 250 mg to about 6000 mg gamma linolenic acid,
- (B) from about 0.4 mg to about 0.9 mg iodine,
- (C) from about 25 µg to about 400 µg of selenium, and
- (D) fat, protein, carbohydrate, or combinations thereof, wherein the amount of protein is within a range of 2 g to about 20 g, wherein the oral nutritional composition provides from about 50 kcal to about 1000 kcal of energy per serving or dose.

53. An oral nutritional composition for improving breast health in women, said composition comprising per serving or dose:
- (A) from about 250 mg to about 6000 mg gamma linolenic acid,
- (B) from about 0.25 mg to about 2.0 mg iodine,
- (C) from about 25 µg to about 400 µg of selenium, and
- (D) fat, protein, carbohydrate, or combinations thereof, wherein the amount of protein is within a range of 2 g to about 20 g, wherein the oral nutritional composition provides from about 50 kcal to about 500 kcal of energy per serving or dose.

* * * * *